US011135250B2

(12) United States Patent
Han

(10) Patent No.: US 11,135,250 B2
(45) Date of Patent: Oct. 5, 2021

(54) MUSCULOSKELETAL STEM CELL

(71) Applicant: CELLATOZ THERAPEUTICS, INC., Seongnam-si (KR)

(72) Inventor: Myung-Kwan Han, Jeonju-si (KR)

(73) Assignee: Cellatoz Therapeutics, Inc., Gyeonggi (KR)

( * ) Notice: Subject to any disclaimer, the term of this patent is extended or adjusted under 35 U.S.C. 154(b) by 0 days.

(21) Appl. No.: 16/630,841

(22) PCT Filed: Oct. 24, 2018

(86) PCT No.: PCT/KR2018/012664
§ 371 (c)(1),
(2) Date: Jan. 13, 2020

(87) PCT Pub. No.: WO2019/083281
PCT Pub. Date: May 2, 2019

(65) Prior Publication Data
US 2021/0009958 A1 Jan. 14, 2021

(30) Foreign Application Priority Data
Oct. 25, 2017 (KR) .......................... 10-2017-0139143

(51) Int. Cl.
| | |
|---|---|
| A61K 35/34 | (2015.01) |
| A61P 19/00 | (2006.01) |
| C12N 5/077 | (2010.01) |
| A61P 21/00 | (2006.01) |
| C12N 5/0775 | (2010.01) |
| G01N 33/569 | (2006.01) |
| A61K 35/32 | (2015.01) |
| C12N 5/00 | (2006.01) |
| C12N 5/0735 | (2010.01) |
| C12N 5/074 | (2010.01) |

(52) U.S. Cl.
CPC .............. *A61K 35/34* (2013.01); *A61K 35/32* (2013.01); *A61P 19/00* (2018.01); *A61P 21/00* (2018.01); *C12N 5/0018* (2013.01); *C12N 5/066* (2013.01); *C12N 5/0606* (2013.01); *C12N 5/0653* (2013.01); *C12N 5/0654* (2013.01); *C12N 5/0655* (2013.01); *C12N 5/0658* (2013.01); *C12N 5/0662* (2013.01); *C12N 5/0696* (2013.01); *G01N 33/56966* (2013.01); *C12N 2501/115* (2013.01); *C12N 2501/15* (2013.01); *C12N 2501/155* (2013.01); *C12N 2501/16* (2013.01); *C12N 2501/235* (2013.01); *C12N 2501/415* (2013.01); *C12N 2501/727* (2013.01); *C12N 2501/998* (2013.01); *C12N 2501/999* (2013.01); *C12N 2506/02* (2013.01); *C12N 2506/13* (2013.01); *C12N 2506/45* (2013.01); *C12N 2533/52* (2013.01); *C12N 2533/54* (2013.01)

(58) Field of Classification Search
CPC .......... A61K 35/34; A61P 19/00; A61P 21/00; C12N 5/0658; C12N 5/0662
See application file for complete search history.

(56) References Cited

U.S. PATENT DOCUMENTS

| | | |
|---|---|---|
| 9,080,147 B2 | 7/2015 | Pera |
| 2005/0079606 A1 | 4/2005 | Tamaki et al. |
| 2008/0213231 A1 | 9/2008 | Oh et al. |
| 2019/0247441 A1 | 8/2019 | Han |

FOREIGN PATENT DOCUMENTS

| | | |
|---|---|---|
| CN | 101641436 A | 2/2010 |
| JP | 2014524258 A | 9/2014 |
| KR | 10200901151 | 11/2009 |
| KR | 100973324 B | 7/2010 |
| WO | WO 03027281 A2 | 4/2003 |
| WO | WO 2007010858 A1 | 1/2007 |
| WO | WO-2014161075 A1 | 10/2014 |
| WO | WO-2016055519 A1 | 4/2016 |
| WO | WO-2017026878 A1 | 2/2017 |
| WO | WO-2019083281 A2 | 5/2019 |

OTHER PUBLICATIONS

Dominici et al., Minimal criteria for defining multipotent mesenchymal stromal cells. The International Society for Cellular Therapy position statement. Cytotherapy, vol. 8, No. 4 (2006) pp. 315-317. (Year: 2006).*
Glaeser et al., "Musculoskeletal stem cells". In: Steinhoff G. (eds) Regenerative Medicine—from Protocol to Patient, Springer Cham. (2016) pp. 315-343. (Year: 2016).*
Caplan, A., "Mesenchymal Stem Cells: Time to Change the Name!," Stem Cells Translation Medicine 6:1445-1451, AlphaMed Pres, United States (2017).
Chan, C., et al., "Identification of the Human Skeletal Stem Cell," Cell 175(1):43-56, Humana Cell Press, United States (2018).
Rifas, L., "The Role of Noggin in Human Mesenchymal Stem Cell Differentiation," Journal of Cellular Biochemistry 100:824-834, Wiley Online Library, United States (2007).
International Search Report in International Patent Application No. PCT/KR2018012664, dated May 10, 2019, Korean Intellectual Property Office, 7 pages.
Extended European Search Report dated Nov. 15, 2019, in European Patent Application No. 191170901.3, Munich, Germany, European Patent Office, 9 pages.

(Continued)

*Primary Examiner* — Kara D Johnson
(74) *Attorney, Agent, or Firm* — Sterne, Kessler, Goldstein & Fox P.L.L.C.

(57) ABSTRACT

The present disclosure relates to a novel musculoskeletal stem cell (MSSC) differentiated from an ESC (embryonic stem cell) or an iPSC (induced pluripotent stem cell). The musculoskeletal stem cell of the present disclosure can be easily induced from a human embryonic stem cell or a human-derived pluripotent stem cell and can be effectively differentiated not only into bone but also into cartilage, tendon and muscle. Accordingly, it can be usefully used for prevention or treatment of various musculoskeletal diseases.

4 Claims, 21 Drawing Sheets

(56) References Cited

OTHER PUBLICATIONS

Bose, B., and Shenoy, P. S., "Pluripotent Conversion of Muscle Stem Cells Without Reprogramming Factors or Small Molecules," *Stem Cell Reviews and Reports* 12(1):73-89, Springer Science+Business Media, United States (Sep. 2015).

Jung, D-W., and Williams, D. R., "Reawakening atlas: chemical approaches to repair or replace dysfunctional musculature," *ACS Chemical Biology* 7(11):1773-1790, American Chemical Society, United States (published online Oct. 2012, published in print Nov. 2012).

Quattrocelli, M., et al., "Mesodermal iPSC-derived progenitor cells functionally regenerate cardiac and skeletal muscle," *Journal of Clinical Investigation* 125(12):4463-4482, The American Society for Clinical Investigation, United States (published online Nov. 2015, published in print Dec. 2015).

\* cited by examiner

MUSCULOSKELETAL STEM CELL

TECHNICAL FIELD

The present disclosure relates to a novel musculoskeletal stem cell capable of differentiating into a musculoskeletal tissue and a method for preparing the same.

BACKGROUND ART

The disease of the musculoskeletal system made up of muscles, bones, joints, etc. causes severe activity limitation, body pain, etc. The degeneration of the functions of muscles, bones and joints with aging is an unavoidable consequence. The diseases occurring frequently as a result of the degeneration of the function of the musculoskeletal system include degenerative arthritis, tendinitis, bone fracture, sprain, sarcopenia, etc. As life expectancy increases recently due to improvement in health care, the number of patients suffering from musculoskeletal diseases is also increasing. However, quality of life is aggravated because healthy aging with healthy musculoskeletal system is not achieved.

Ossification is the process of bone formation. There are two processes of bone formation: intramembranous ossification and endochondral ossification. Intramembranous ossification is the direct conversion of mesenchymal tissue into bone and occurs inside the skull, while endochondral ossification involves the formation of cartilage tissue from aggregated mesenchymal cells followed by conversion of the cartilage tissue into bone. This ossification process is essential mostly in the bone formation of vertebrates.

Human embryonic stem cells (hESCs) are pluripotent cells that can grow without limitation and can differentiate into any cell type. hESCs are useful tools for the study of embryonic development in cellular level and for the cell replacement therapy. hESCs can differentiate into specific tissues including skeletal tissues such as bone and cartilage and, therefore, may be used for the restoration of skeletal tissues.

Human-induced pluripotent stem cells (hiPSCs) are known as pluripotent stem cells that can differentiate into any type of cells. hiPSCs are useful for the study of embryonic development in cellular level and are drawing attentions as cell therapeutic agents. Because these cells can be differentiated into skeletal tissue, e.g., bone or cartilage, through transplantation, they may be usefully used for the restoration and treatment of damaged skeletal tissue.

Mesenchymal stem cells (MSCs) are the cells that can self-renew and can differentiate into cells of mesenchymal origin such as osteoblasts, adipocytes and cartilage cells. MSCs are used in clinical trials under various conditions and are attempted for trauma, skeletal diseases, graft-versus-host disease following the receipt of bone marrow transplantation, cardiovascular diseases, autoimmune diseases, liver diseases, etc. However, it is very difficult to attain the MSCs in an amount sufficient for therapeutic application. In addition, the mesenchymal stem cells cannot directly differentiate into these tissues in the body in the absence of the in-vitro predifferentiation process of differentiating into bone cartilage or fat using growth factors, vitamins, etc. It is known that the mesenchymal stem cells indirectly facilitate the regeneration of damaged tissues by stimulating intrinsic stem cells by secreting various biofactors, rather than by participating directly in the differentiation into mesenchymal tissues including the musculoskeletal tissues (*Stem Cells Transl Med.* 6(6):1445-1451, 2017).

Accordingly, the necessity of researches on cells that can overcome the limitations of mesenchymal stem cells and can differentiate directly into bone, cartilage, ligaments and muscles in the body is increasing.

The foregoing is intended merely to aid in the understanding of the background of the present disclosure and is not intended to mean that the present disclosure falls within the purview of the related art that is already known to those of ordinary skill in the art.

DISCLOSURE

Technical Problem

The inventors of the present disclosure have identified that a musculoskeletal stem cell (hMSSC) can be derived from a human embryonic stem cell (hESC) or a human-derived pluripotent stem cell (hiPSC) and that the musculoskeletal stem cell can differentiate into bone through endochondral ossification as well as into musculoskeletal tissues such as cartilage, tendon, muscle, etc., thereby completing the present disclosure.

The present disclosure is directed to providing a medium composition for inducing differentiation into a musculoskeletal stem cell.

The present disclosure is also directed to providing a method for preparing a musculoskeletal stem cell, including a step of culturing an ESC or an iPSC in the medium.

The present disclosure is also directed to providing a musculoskeletal stem cell differentiated from an ESC or an iPSC.

The present disclosure is also directed to providing a pharmaceutical composition for preventing or treating a musculoskeletal disease, which contains the musculoskeletal stem cell.

The present disclosure is also directed to providing a method for screening the musculoskeletal stem cell.

Other objects and advantages of the present disclosure will be more apparent from the following detailed description, claims and drawings.

Technical Solution

In an aspect, the present disclosure provides a medium composition for inducing differentiation into a musculoskeletal stem cell (MSSC), which contains noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor.

The inventors of the present disclosure have identified an optimal medium composition capable of inducing a musculoskeletal stem cell (hMSSC) from a human embryonic stem cell or a human-derived pluripotent stem cell and that the musculoskeletal stem cell can differentiate into bone through endochondral ossification as well as into musculoskeletal tissues such as cartilage, tendon, muscle, etc., thereby completing the present disclosure.

In the present disclosure, the term "stem cell" refers to an undifferentiated cell capable of differentiating into various body tissues. The stem cells may be classified into totipotent stem cells, pluripotent stem cells, multipotent stem cells, etc. The term stem cell may be used interchangeably with the terms precursor cell, progenitor cell, etc. In the present disclosure, the stem cell may be an embryonic stem cell (ESC), an induced pluripotent stem cell (iPSC) or a mesenchymal stem cell (MSC). Accordingly, the medium composition of the present disclosure may be used to induce the differentiation of an embryonic stem cell, an induced pluripotent stem cell, etc. into a musculoskeletal stem cell.

The embryonic stem cell is a pluripotent cell derived from all the three germ layers, having capacity for unlimited proliferation without transformation and self-renewal, although not being limited thereto.

In the present disclosure, the term "musculoskeletal stem cell" refers to a cell that can differentiate into bone, cartilage, a tendon, a ligament or muscle without limitation.

The term "differentiation" refers to the process wherein the structure or function of a cell is specialized while the cell grows through division and proliferation, i.e., the process wherein the form or function changes to perform the task assigned to the cell, tissue, etc. of an organism. In general, it refers to a phenomenon where a relatively simple system is split into two or more qualitatively different subsystems. That is to say, the differentiation refers to the variation of the parts of an initially substantially homogenous biological system or the division to qualitatively different parts or subsystems as a result thereof, for example, the division of head, body, etc. from an initially homogeneous egg during ontogeny.

The embryonic stem cell or induced pluripotent stem cell used in the present disclosure is derived from human, cow, horse, goat, sheep, dog, cat, mouse, rat, bird, etc., specifically from human.

Specifically, the Wnt signaling activator of the present disclosure may be SB216763 (3-(2,4-dichlorophenyl)-4-(1-methyl-1H-indol-3-yl)-1H-pyrrole-2,5-dione), SB415286 (3-[(3-chloro-4-hydroxyphenyl)amino]-4-(2-nitrophenyl)-1H-pyrrole-2,5-dione), kenpaullone (9-bromo-7,12-dihydro-indolo[3,2-d]-[1]benzazepin-6(5H)-one), CHIR99021 (9-bromo-7,12-dihydro-pyrido[3',2':2,3]azepino[4,5-b]indol-6(5H)-one), CP21R7 (3-(3-amino-phenyl)-4-(1-methyl-1H-indol-3-yl)-pyrrole-2,5-dione), SB203580 (4-(4-fluorophenyl)-2-(4-methylsulfinylphenyl)-5-(4-pyridyl)-1H-imidazole), H-89 (5-isoquinolinesulfonamide), purmorphamine (2-(1-naphthoxy)-6-(4-morpholinoanilino)-9-cyclohexylpurine) or IQ-1 (2-(4-acetyl-phenylazo)-2-[3,3-dimethyl-3,4-dihydro-2H-isoquinolin-(1E)-ylidene]-acetamide), although not being limited thereto.

Specifically, the ERK signaling inhibitor of the present disclosure may be AS703026 (N-[(2S)-2,3-dihydroxypropyl]-3-[(2-fluoro-4-iodophenyl)amino]-isonicotinamide), AZD6244 (6-(4-bromo-2-chloroanilino)-7-fluoro-N-(2-hydroxyethoxy)-3-methylbenzimidazole-5-carboxamide), PD0325901 (N-[(2R)-2,3-dihydroxypropoxy]-3,4-difluoro-2-[(2-fluoro-4-iodophenyl)amino]-benzamide), ARRY-438162 (5-[(4-bromo-2-fluorophenyl)amino]-4-fluoro-N-(2-hydroxyethoxy)-1-methyl-1H-benzimidazole-6-carboxamide), RDEA119 ((S)—N-(3,4-difluoro-2-((2-fluoro-4-iodophenyl)amino)-6-methoxyphenyl)-1-(2,3-dihydroxypropyl)cyclopropane-1-sulfonamide), GDC0973 ([3,4-difluoro-2-(2-fluoro-4-iodoanilino)phenyl]-3-hydroxy-3-[(2S)-piperidin-2-yl]-azetidin-1-yl-methanone), TAK-733 ((R)-3-(2,3-dihydroxypropyl)-6-fluoro-5-(2-fluoro-4-iodophenylamino)-8-methylpyrido[2,3-d]pyrimidine-4,7(3H,8H)-dione), RO5126766 (3-[[3-fluoro-2-(methylsulfamoylamino)-4-pyridyl]methyl]-4-methyl-7-pyrimidin-2-yloxy chromen-2-one) or XL-518 ([3,4-difluoro-2-[(2-fluoro-4-iodophenyl)amino]phenyl][3-hydroxy-3-[(2S)-2-piperidinyl]-1-azetidinyl]methanone), although not being limited thereto.

Specifically, the TGF-β/activin/nodal signaling inhibitor of the present disclosure may be E-616452 (2-[3-(6-methyl-2-pyridinyl)-1H-pyrazol-4-yl]-1,5-naphthyridine), A-83-01 (3-(6-methyl-2-pyridinyl)-N-phenyl-4-(4-quinolinyl)-1H-pyrazole-1-carbothioamide) or SB431542 (4-[4-(1,3-benzodioxol-5-yl)-5-(2-pyridinyl)-1H-imidazol-2-yl]benzamide), although not being limited thereto.

In an example of the present disclosure, differentiation capacity was compared for media wherein one of the constitutional ingredients noggin, LIF (leukemia inhibitory factor), bFGF (basic fibroblast growth factor), Wnt signaling activator, ERK (extracellular signal-regulated kinase) signaling inhibitor and TGF-β/activin/nodal signaling inhibitor was absent with a medium containing all the constitutional ingredients. As a result, it was confirmed that differentiation into cartilage (Alcian blue) or bone (ALP and Alizarin red S) was not achieved well when any of the constitutional ingredients was deficient (FIG. 7, Table 3).

Also, when the medium was replaced with one to which a conditioned medium (a culture supernatant obtained after culturing CF1 mouse embryonic fibroblasts with a medium obtained by replacing DMEM/F12 in a complete medium with knockout DMEM (supplemented with 20% knockout serum replacement (Invitrogen, USA), 1 mM glutamine, 1% nonessential amino acids (Invitrogen, USA), 0.1 mM β-mercaptoethanol, 0.1% penicillin-streptomycin and 5 mg/mL bovine serum albumin)) was added in place of noggin and the differentiation capacity was compared, it was confirmed that the medium composition of the present disclosure using noggin increased the tendency for osteogenic differentiation 10-fold or higher and increased the differentiation speed by 1-2 weeks (Tables 1 and 2).

In another aspect, the present disclosure provides a method for preparing a musculoskeletal stem cell, including a step of culturing an ESC (embryonic stem cell) or an iPS (induced pluripotent stem cell) in the medium composition for inducing differentiation into a musculoskeletal stem cell.

The culturing may performed for 5 passages or longer, specifically for 5-25 passages, more specifically for 7-18 passages, without change in the composition of the medium.

In an example of the present disclosure, it was confirmed that the musculoskeletal stem cells differentiated by culturing human embryonic stem cells or human-derived pluripotent stem cells for 7 passages or longer using the medium for inducing differentiation into a musculoskeletal stem cell according to the above method were stably identical. They grew with similar morphologies for 10 passages or longer, from passage 7 to passage 17, and showed a positive response to staining with the aging marker β-galactosidase since passage 19, suggesting that aging was progressed (FIG. 1A).

In another aspect, the present disclosure provides a musculoskeletal stem cell prepared using the medium composition for inducing differentiation into a musculoskeletal stem cell.

In another aspect, the present disclosure provides a musculoskeletal stem cell (MSSC) differentiated from an ESC (embryonic stem cell) or an iPSC (induced pluripotent stem cell).

In a specific exemplary embodiment of the present disclosure, the musculoskeletal stem cell of the present disclosure has the following characteristics:
  a) positive for the ectodermal marker nestin (NES);
  b) positive for the myogenic satellite marker Pax7;
  c) positive for the mesodermal marker α-SMA;
  d) negative for the pluripotency marker LIN28; and
  f) negative for the mesenchymal stem cell marker CD90.

In a specific exemplary embodiment of the present disclosure, the musculoskeletal stem cell of the present disclosure further has the following characteristic: negative for the mesenchymal stem cell marker CD271.

In a specific exemplary embodiment of the present disclosure, the musculoskeletal stem cell of the present disclosure further has the following characteristic: positive for the pluripotency marker DPPA4.

In a specific exemplary embodiment of the present disclosure, the musculoskeletal stem cell of the present disclosure further has the following characteristic: negative for the mesodermal markers T and nodal.

In a specific exemplary embodiment of the present disclosure, the musculoskeletal stem cell of the present disclosure has the following characteristic: positive for the neuroectodermal marker Pax6.

In a specific exemplary embodiment of the present disclosure, the musculoskeletal stem cell of the present disclosure has the following characteristic: positive for the intestinal stem cell marker LGR5.

In a specific exemplary embodiment of the present disclosure, the musculoskeletal stem cell of the present disclosure has the following characteristic: negative for the chondrocyte marker SOX9.

In a specific exemplary embodiment of the present disclosure, the musculoskeletal stem cell of the present disclosure has the following characteristic: negative for the myoblast marker MyoD.

In a specific exemplary embodiment of the present disclosure, the musculoskeletal stem cell of the present disclosure is positive for CD10, CD44, CD105, CD146 and/or CD166.

In an example of the present disclosure, the expression of most pluripotency markers was not observed in the musculoskeletal stem cells of the present disclosure but the expression of DPPA4 was observed and the cells were positive for the ectodermal marker NES. In addition, they were positive for most mesodermal markers except DES and the early mesodermal markers T and nodal and negative for most endodermal markers (FIG. 1C). In addition, when the expression of mesenchymal stem cell-specific cell surface antigens was investigated for hMSSC, among the mesenchymal stem cell markers, CD44, CD51, CD73, CD105, CD146 and CD166 were expressed in the hMSSC but CD90 and CD271 were not expressed in the hMSSC. In addition, whereas the vascular cell surface markers CD2, CD3, CD7, CD8, CD11b, CD14, CD19, CD20, CD31, CD34 and CD56 were not expressed, the pre-B cell marker CD10 was expressed (FIG. 1D). Additionally, when the expression of various tissue-specific markers was investigated, the mesodermal marker alpha smooth muscle actin (α-SMA), the neuroectodermal marker Pax6, the myogenic satellite marker Pax7, the intestinal stem cell marker LGR5, etc. were expressed and the chondrocyte marker SOX9, the myoblast marker MyoD, etc. were not expressed (FIG. 1F).

In a specific exemplary embodiment of the present disclosure, the musculoskeletal stem cell is differentiated into the mesoderm but not is differentiated into the ectoderm or endoderm.

In a specific exemplary embodiment of the present disclosure, the musculoskeletal stem cell is differentiated into muscle, bone, cartilage, a tendon or a ligament.

In an example of the present disclosure, when the musculoskeletal stem cell of the present disclosures were cultured in a medium for culturing a mesenchymal stem cell (e.g., MSCGM, MSCGM-CD, etc.) and were transplanted into the kidney capsule or hypoderm, the typical formation of muscle, fat, tendon, bone and cartilage was observed in the kidney or hypoderm (FIG. 3). All the differentiated muscle muscles were differentiated into skeletal muscle, not into smooth muscle. It was also confirmed in the in-vivo experiment that they could be differentiated into fat, although the differentiation into fat was not observed in the in-vitro experiment.

In a specific exemplary embodiment of the present disclosure, the musculoskeletal stem cell is not differentiated into a nerve.

In an example of the present disclosure, when the musculoskeletal stem cells were differentiated into nerve cells in a medium for inducing differentiation into a nerve and investigated using a nerve cell marker, it was confirmed that the musculoskeletal stem cell does not have the potential to differentiate into a nerve cell (FIG. 2E).

In a specific exemplary embodiment of the present disclosure, the musculoskeletal stem cell is not differentiated into an endothelial cell.

In an example of the present disclosure, when the musculoskeletal stem cells were differentiated into endothelial cells in a medium for inducing differentiation into an EC (endothelial growth medium) and investigated using an endothelial cell marker, it was confirmed that the musculoskeletal stem cell does not have the potential to differentiate into an endothelial cell (FIGS. 2C and 2D).

The musculoskeletal stem cell was deposited in the Korean Cell Line Bank on Oct. 10, 2018 and was given the accession number KCLRF-BP-00460.

In another aspect, the present disclosure provides a pharmaceutical composition for preventing or treating a musculoskeletal disease, which contains the musculoskeletal stem cell.

In another aspect, the present disclosure provides a cell therapeutic agent, which contains the musculoskeletal stem cell.

In another aspect, the present disclosure provides a use of a pharmaceutical composition for preventing or treating a musculoskeletal disease, which contains the musculoskeletal stem cell.

In another aspect, the present disclosure provides a method for preventing or treating a musculoskeletal disease, which includes a step of administering the musculoskeletal stem cell to a patient.

The musculoskeletal disease of the present disclosure may be specifically one or more disease selected from a group consisting of osteoporosis, osteomalacia, osteogenesis imperfecta, osteopetrosis, osteosclerosis, Paget's disease, bone cancer, arthritis, rickets, fracture, periodontal disease, segmental bone defect, osteolytic bone disease, primary and secondary hyperparathyroidism, hyperostosis, degenerative arthritis, degenerative knee joint disease, degenerative hip joint disease, degenerative foot joint disease, degenerative hand joint disease, degenerative shoulder joint disease, degenerative elbow joint disease, chondromalacia patellae, simple knee arthritis, osteochondritis dissecans, lateral epicondylitis, medial epicondylitis, Heberden's nodes, Bouchard's nodes, degenerative thumb CM arthrosis, meniscal injury, degenerative disc disease, cruciate ligament injury, biceps brachii muscle injury, ligament injury, tendon injury, frozen shoulder, rotator cuff tear, calcific tendinitis, shoulder impingement syndrome, recurrent dislocation, habitual dislocation, senile sarcopenia and muscular dystrophy, although not being limited thereto.

The pharmaceutical composition of the present disclosure may contain a pharmaceutically acceptable carrier. The pharmaceutically acceptable carrier contained in the composition may be one commonly used for preparation, including lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition may further contain a lubricant, a humectant, a sweetener, a flavorant, an emulsifier, a suspending agent, a preservative, etc., in addition to the above ingredients.

The pharmaceutical composition of the present disclosure may be administered orally or parenterally. For parenteral administration, it may be administered via intravenous injection, subcutaneous injection, intramuscular injection, intraarticular injection, intraosseous infusion, intraperitoneal injection, endothelial administration, topical administration, intranasal administration, intrapulmonary administration, intrarectal administration, etc. Also, the composition may be administered by any device capable of delivering the active ingredient to a target cell.

An appropriate administration dosage of the pharmaceutical composition of the present disclosure may be determined in consideration of various factors such as formulation method, administration mode, the age, body weight and sex of a patient, pathological condition, diet, administration time, administration route, excretion rate and response sensitivity. Specifically, the appropriate administration dosage of the composition may be $10^2$-$10^{10}$ cells/kg for an adult. The term pharmaceutically effective amount refers to an amount enough for preventing or treating a musculoskeletal disease.

The composition of the present disclosure may be prepared into a single- or multiple-dose unit formulation using a pharmaceutically acceptable carrier and/or excipient according to a method that can be easily carried out by those skilled in the art. The formulation may be in the form of a solution in an oily or aqueous medium, a suspension, a syrup, an emulsion, an extract, a powder, a granule, a tablet or a capsule and may further contain a dispersant or a stabilizer. In addition, the composition may be administered either independently or in combination with other therapeutic agent(s) and they may be administered either sequentially or simultaneously. Also, it may be administered as a single dose or repeatedly as desired.

In the present disclosure, the term "cell therapeutic agent" refers to medication used for therapeutic, diagnostic and preventive purposes, which contains a cell or tissue isolated from human and cultured and prepared through special operation (as provided by the USFDA). It is a medication used for therapeutic, diagnostic and preventive purposes through a series of actions of in-vitro multiplication and screening of living autologous, allogenic and xenogenic cells or changing of the biological characteristics of cells by other means for recovering the functions of cells or tissues.

In the present disclosure, the term "prevention" refers to any action of inhibiting a musculoskeletal disease or delaying the progression thereof by administering the composition or cell therapeutic agent of the present disclosure.

In the present disclosure, the term "treatment" refers to any action of improving or favorably changing a musculoskeletal disease by administering the composition or cell therapeutic agent of the present disclosure.

The pharmaceutical composition or cell therapeutic agent of the present disclosure may be used for human or an animal.

The pharmaceutical composition or cell therapeutic agent of the present disclosure may be used either alone or in combination with surgery, radiotherapy, hormone therapy, chemotherapy, a biological response modifier, implantation, insertion of an artificial joint, artificial cartilage, etc., regeneration therapy, etc., for prevention and treatment of a musculoskeletal disease.

In another aspect, the present disclosure provides a method for screening a musculoskeletal stem cell.

In a specific exemplary embodiment of the present disclosure, the method includes a step of screening a cell having the following characteristics:
a) positive for the ectodermal marker nestin (NES);
b) positive for the myogenic satellite marker Pax7;
c) positive for the mesodermal marker α-SMA;
d) negative for the pluripotency marker LIN28; and
f) negative for the mesenchymal stem cell marker CD90.

In a specific exemplary embodiment of the present disclosure, the method further includes a step of screening a cell having the following characteristic: negative for the mesenchymal stem cell marker CD271.

In a specific exemplary embodiment of the present disclosure, the method further includes a step of screening a cell having the following characteristic: positive for the pluripotency marker DPPA4.

In a specific exemplary embodiment of the present disclosure, the method further includes a step of screening a cell having the following characteristic: negative for the mesodermal markers T and nodal.

In a specific exemplary embodiment of the present disclosure, the method further includes a step of screening a cell having the following characteristic: positive for the neuroectodermal marker Pax6.

In a specific exemplary embodiment of the present disclosure, the method further includes a step of screening a cell having the following characteristic: positive for the intestinal stem cell marker LGR5.

In a specific exemplary embodiment of the present disclosure, the method further includes a step of screening a cell having the following characteristic: negative for the chondrocyte marker SOX9.

In a specific exemplary embodiment of the present disclosure, the method further includes a step of screening a cell having the following characteristic: negative for the myoblast marker MyoD.

In a specific exemplary embodiment of the present disclosure, the method further includes a step of screening a cell positive for CD10, CD44, CD105, CD146 and/or CD166.

By using the screening method of the present disclosure, a musculoskeletal stem cell capable of being differentiated effectively to bone, cartilage, a tendon, a ligament, muscle, etc. may be screened easily.

Advantageous Effects

The features and advantages of the present disclosure may be summarized as follows.

(i) The present disclosure provides a musculoskeletal stem cell derived from an ESC or an iPSC.

(ii) Also, the present disclosure provides a method for preparing a musculoskeletal stem cell, which includes a step of culturing an ESC or an iPS in a medium containing noggin, LIF, bFGF, etc.

(iii) The musculoskeletal stem cell of the present disclosure can be easily induced from a human embryonic stem cell or a human-derived pluripotent stem cell and may be differentiated effectively into bone, cartilage, a tendon or muscle. Therefore, it can be usefully used for the prevention or treatment of various musculoskeletal diseases.

BRIEF DESCRIPTION OF DRAWINGS

FIG. 1A shows the change in cell morphology of hESC subcultured with a medium for inducing differentiation into a musculoskeletal stem cell, from passage 7 to passage 19. FIG. 1B shows a result of observing the expression of the pluripotency markers OCT4, NANOG, SOX2 and LIN28 in hMSSC by immunocytochemistry. FIG. 1C shows a result of confirming the expression of pluripotency, ectodermal, mesodermal and endodermal markers in hESC, hMSC and hMSSC at passages 7 and 17 by RNA sequencing, twice respectively. FIG. 1D shows a result of measuring the expression of cell surface antigens by flow cytometry for characterization of hMSSC. FIG. 1E shows a result of analyzing the expression of various cell-specific markers by immunocytochemistry for characterization of hMSSC. In the figure, DAPI represents stained nuclei and the blue triangle indicates a β-galactosidase positive cell.

FIG. 2A shows a result of comparing the in-vitro bone, cartilage and fat differentiation capacity of hMSC and hMSSC. FIG. 2B shows a result of confirming that hMSSC has the potential to differentiate into skeletal muscle by immunocytochemistry for the skeletal muscle cell-specific marker MYH9. C2C12 was used as a positive control group for the skeletal muscle cell. FIGS. 2C and 2D show a result of confirming that hMSSC lacks the potential to differentiate into an endothelial cell by immunocytochemistry for the endothelial cell-specific markers CD31 and VE-cadherin. FIG. 2E shows a result of confirming that hMSSC lacks the potential to differentiate into a nerve cell by immunocytochemistry for the nerve cell-specific marker MAP2. As a positive control group, neural stem cells differentiated from H9 hESC were used.

FIG. 3A-a shows that muscle, fat and tendon were formed when hMSSC was transplanted into the kidney as confirmed by H&E staining. FIG. 3A-b shows a result of confirming the differentiation of hMSSC transplanted into the kidney into muscle, fat and tendon cells by immunohistochemistry for the muscle-specific marker pMLC, the fat-specific marker PPARgamma (PPAr) and ligament-specific marker Scx. hLA is a human cell-specific marker. The staining result shows that the cell is derived from human. FIG. 3B-a shows a result of micro-CT scanning showing that bone was formed at the site where hMSSC was transplanted into the kidney. FIGS. 3B-b and 3B-c show a result of confirming bone formation by H&E and pentachrome immunohistochemical staining. FIG. 3B-d shows a result of confirming the expression of the human cell marker hLA (human leukocyte antigen), the bone markers Osx (osterix), Runx2, DMP1 and OCN (osteocalin) and the vascular marker vWF in the cells of the osteoblastic tissue by immunohistochemistry. FIG. 3C shows a result of confirming that cartilage was formed as a result of differentiation of hMSSC transplanted into the hypoderm into cartilage cells by H&E and toluidine blue immunohistochemical staining. The expression of the cartilage marker ColII (collagen II) was also confirmed by immunohistochemistry.

FIG. 4A shows that, when hMSC was transplanted into the fracture site, bone was formed by the cells of mouse itself, not by the hMSC. FIG. 4A-a shows micro-CT images obtained 2, 4 and 6 weeks after the transplantation of hMSC into the fracture site. FIG. 4A-b shows a result of H&E immunohistochemistry of the thighbone containing the fracture site into which hMSC was transplanted. FIG. 4A-c shows a result of magnifying the red square portion of 4A-b. FIG. 4A-d shows a result of confirming that the transplanted hMSC was not differentiated into bone cells by immunohistochemistry for the bone cell marker Runx2 and the human cell marker hLA. FIG. 4B shows that, unlike hMSC, bone was formed as transplanted hMSSC was differentiated. FIG. 4B-a shows micro-CT images obtained 2, 4 and 6 weeks after the transplantation of hMSSC into the fracture site. FIG. 4B-b shows a result of H&E immunohistochemistry of the thighbone containing the fracture site into which hMSSC was transplanted. FIG. 4B-c shows a result of magnifying the red square portion of 4B-b. FIG. 4B-d shows a result of confirming that the transplanted hMSSC was differentiated into bone cells by immunohistochemistry for the bone cell marker Runx2 and the human cell marker hLA.

FIG. 5A shows a result of confirming the expression level of the pluripotency markers Oct4, Nanog, Sox2 and Lin28 in hMSSC differentiated from hiPS by immunocytochemistry. FIG. 5B shows a result of investigating the expression of specific cell surface antigens in hMSSC differentiated from hiPS by flow cytometry. FIG. 5C shows a result of confirming the in-vitro bone, cartilage and fat differentiation capacity of hMSSC differentiated from hiPS. FIG. 5D shows a result of differentiating hMSSC differentiated from hiPS into skeletal muscles in a medium for inducing differentiation into skeletal muscle and then conducting immunocytochemistry for the skeletal muscle marker MYH9.

MODE FOR INVENTION

Figure 1A:
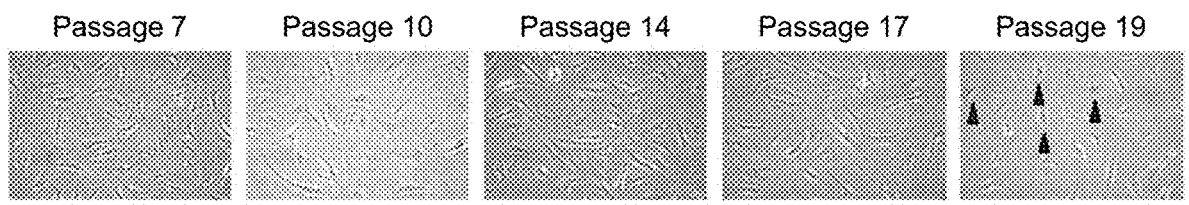
FIGS. 1A-1E show the characteristics of hMSSC differentiated from hESC.

Hereinafter, the present disclosure will be described in detail through examples. However, the following examples are for illustrative purposes only and it will be apparent to those of ordinary skill in the art that the scope of the present disclosure is not limited by the examples.

EXAMPLES

Experimental Materials and Methods

Example 1

Experimental Animals 7- to 10-week-old Balb/c-nude background mice (weighing 20-24 g) were purchased from Orient Bio (Seongnam, Korea). All animal experiments were performed according to the guidelines of the Chonbuk University Animal Care and Use Committee. The animals were accommodated under controlled-temperature (21-24° C.) and 12:12-hr light-darky cycle environments and were given free access to water and feed.

Example 2.1

Induction of Differentiation from hESC into hMSSC

H9 hESCs (human embryonic stem cells) were purchased from WiCell (Madison, Mich., USA). The hESCs were cultured on CF1 mouse embryonic fibroblast (MEF) feeder cells whose cell division was blocked by mitomycin C treatment. A hESC culture medium was prepared as DMEM/F12 (Invitrogen, USA) supplemented with 20% knockout serum replacement (KSR; Invitrogen, USA), 1 mM glutamine (Invitrogen, USA), 1% nonessential amino acids (Invitrogen, USA), 0.1 mM β-mercaptoethanol (Invitrogen, USA), 0.1% penicillin/streptomycin (Invitrogen, USA) and 15 ng/mL bFGF (R&D Systems, USA).

The hESCs were induced to differentiate into hMSSCs (human musculoskeletal stem cells) using a medium for inducing differentiation into MSSC (hereinafter, referred to as "MSSC medium") of the following composition:
1) 250 ng/mL human noggin (KOMA Biotech, Korea),
2) 20 ng/mL human LIF (KOMA Biotech, Korea),
3) 15 ng/mL basic fibroblast growth factor (FGF) (R&D Systems, USA) (FGF2 signaling activator),
4) 3 µM CHIR99021 (Cayman, USA) (Wnt signaling activator),
5) 1 µM PD0325901 (Cayman, USA) (ERK (extracellular signal-regulated kinase) signaling inhibitor),
6) 10 µM SB431542 (Tocris, United Kingdom) (TGF-β/activin/nodal signaling inhibitor) and
7) 10% knockout serum replacement (Invitrogen, USA), 1% N2 supplement (Gibco, USA), 2% B27 supplement (Gibco, USA), 1% nonessential amino acids (Gibco, USA), 43% DMEM/F12 (Gibco, USA), 43% Neurobasal (Gibco, USA), 1 mM glutamine, 0.1 mM β-mercaptoethanol, 0.1% penicillin-streptomycin and 5 mg/mL bovine serum albumin (Gibco, USA).

After treating the hESCs with ROCK (Rho-associated coiled-coil kinase) inhibitor (Y-27632, 10 µM, Calbiochem, Germany) and PKC (protein kinase C) inhibitor (Go6983, 2.5 µM, Sigma, USA) for 24 hours in order to enhance survivability and trypsinizing the hESCs by treating with TrypLE (Life Technologies, USA), they were induced to differentiate into hMSSCs by culturing with the MSSC medium on a culture dish coated with vitronectin and gelatin (1 ng/mL, Sigma, USA) until passage 7. The differentiated MSSC cells were identified to be stably identical from passage 5 and the cells cultured for 10 passages were deposited in the Korean Cell Line Bank on Oct. 10, 2018 and were given the accession number KCLRF-BP-00460.

Example 2.2

Induction of Differentiation from hiPSC into hMSSC hiPSCs (human induced pluripotent stem cells) were obtained by introducing the OCT4, KLF4, SOX2 and cMYC genes to BJ fibroblasts (ATCC®CRL2522™) using Sendai virus according to the method developed by Hasegawa et al. (Fusaki et al., 2009, PNAS 85, 348-362). The hiPSCs were cultured on CF1 mouse embryonic fibroblast (MEF) feeder cells whose cell division was blocked by mitomycin C treatment. A hiPSC culture medium was prepared as DMEM/F12 (Invitrogen, USA) supplemented with 20% knockout serum replacement (KSR; Invitrogen, USA), 1 mM glutamine (Invitrogen, USA), 1% nonessential amino acids (Invitrogen, USA), 0.1 mM β-mercaptoethanol (Invitrogen, USA), 0.1% penicillin/streptomycin (Invitrogen, USA) and 15 ng/mL bFGF (R&D Systems, USA).

The hESCs were induced to differentiate into hMSSCs (human musculoskeletal stem cells) using a medium for inducing differentiation into MSSC (hereinafter, referred to as "MSSC medium") of the following composition:
1) 250 ng/mL human noggin (KOMA Biotech, Korea),
2) 20 ng/mL human LIF (KOMA Biotech, Korea),
3) 15 ng/mL basic fibroblast growth factor (FGF) (R&D Systems, USA) (FGF2 signaling activator),
4) 3 µM CHIR99021 (Cayman, USA) (Wnt signaling activator),
5) 1 µM PD0325901 (Cayman, USA) (ERK (extracellular signal-regulated kinase) signaling inhibitor),
6) 10 µM SB431542 (Tocris, United Kingdom) (TGF-β/activin/nodal signaling inhibitor) and
7) 10% knockout serum replacement (Invitrogen, USA), 1% N2 supplement (Gibco, USA), 2% B27 supplement (Gibco, USA), 1% nonessential amino acids (Gibco, USA), 43% DMEM/F12 (Gibco, USA), 43% Neurobasal (Gibco, USA), 1 mM glutamine, 0.1 mM β-mercaptoethanol, 0.1% penicillin-streptomycin and 5 mg/mL bovine serum albumin (Gibco, USA).

After treating the hiPSCs with ROCK (Rho-associated coiled-coil kinase) inhibitor (Y-27632, 10 µM, Calbiochem, Germany) and PKC (protein kinase C) inhibitor (Go6983, 2.5 µM, Sigma, USA) for 24 hours in order to enhance survivability and trypsinizing the hiPSCs by treating with TrypLE (Life Technologies, USA), they were induced to differentiate into hMSSCs by culturing with the MSSC medium on a culture dish coated with vitronectin and gelatin (1 ng/mL, Sigma, USA) until passage 7. The differentiated MSSC cells were identified to be stably identical from passage 5.

Example 3

Immunohistochemistry

Samples obtained by injecting the hMSSCs differentiated in Example 2.1 into the hypoderm and kidney of Balb/c-nude as described in Examples 10.1 and 10.2 were fixed overnight at 4° C. in 2% paraformaldehyde (PFA; Wako, Japan). For a sample to investigate differentiation into bone, decalcification was conducted at 4° C. for 2 weeks in PBS (pH 7.2) using 0.4 M EDTA. Then, the samples were dehydrated using ethanol and xylene sequentially, embedded in paraffin and cut to 5 µm thickness. The cut surface was stained with H&E and modified Movat's pentachrome (Cosmobio, Japan).

Example 4

RNA Sequencing

RNAs were extracted from H9 hESCs, human mesenchymal stem cells (hMSCs; Lonza, Switzerland) and the hMSSCs of Example 2.1 using Trizol reagent (Invitrogen, USA). The RNA quality was evaluated with the Agilent 2100 bioanalyzer and the RNA 6000 Nano Chip (Agilent Technologies, USA) and quantification was performed using the ND-2000 spectrophotometer (Thermo Inc., USA). An RNA library for RNA sequencing was established using the SENSE 3' mRNA-Seq Library Prep Kit (Lexogen Inc., Australia). RNA sequencing was conducted using NextSeq 500 (Illumina Inc., USA). The SENSE 3' mRNA-Seq reads were aligned using Bowtie2 version 2.1.0. The difference in gene expression was determined using Bioconductor R version 3.2.2 with EdgeR. The read count data were processed with Genowiz version 4.0.5.6 (Ocium Biosolutions, USA).

Example 5

Immunochemistry

"Immunocytochemistry" was performed according to the following method.

For immunofluorescence staining, the cells were fixed in 4% paraformaldehyde, made permeable with 0.5% Triton X-100 and then blocked with 10% normal goat, normal rabbit or fetal bovine serum in phosphate-buffered saline (PBS). The sample was stained overnight at 4° C. with primary antibodies against Tuj1 (Covance, USA), α-smooth muscle (α-SMA, Sigma, USA), Nanog (Santa Cruz, USA), Oct3/4 (Santa Cruz, USA), Sox2 (Santa Cruz, USA), CD31 (DAKO, Japan), vascular endothelial-cadherin (R&D, USA), MYH9 (Santa Cruz, USA), HNK-1 (Santa Cruz, USA) and MAP-2 (Santa Cruz, USA). Then, the cells were stained with the secondary antibodies Alexa Fluor 488-goat anti-mouse IgG, Alexa Fluor 594-donkey anti-rabbit IgG, Alexa Fluor 488-donkey anti-rabbit IgG and Alexa Fluor 594-donkey anti-mouse IgG (Invitrogen, USA). Then, the cell nuclei were stained with DAPI (4,6-diamidino-2-phenylindole). Then, images were obtained using the Olympus IX71 optical microscope and the MetaMorph software (Molecular Devices, USA).

"Immunohistochemistry" was performed according to the following method.

Tissues were fixed overnight at 4° C. with 4% PFA (Wako, Japan) in PBS. All samples were decalcified with Morse's solution. The samples were dehydrated sequentially with ethanol and xylene, embedded in paraffin (Leica Biosystems, Germany) and then cut to 5 µm thickness. After blocking the cut surface for 15 minutes in 3% hydrogen peroxide, the samples were incubated at 4° C. overnight with primary antibodies. The primary antibodies treated on the cut surface are as follows: mouse monoclonal antibody against HLA class I (Abcam, United Kingdom), goat polyclonal antibody against collagen type II (Santacruz, USA), rabbit polyclonal antibody against osteocalcin (Santacruz, USA), osterix (Abcam, USA), phospho-myosin light chain (pMLC) (Abcam, USA), scleraxis (Antibodies Online, USA), PPARgamma (PPAr) (Santacruz, USA) Runx2 (Novus, USA), DMP1 (Santacruz, USA), vWF (Santacruz, USA) and sclerostin (Santacruz, USA). The used secondary antibodies were Alexa 555 (Invitrogen, USA) and Alexa 488 (Invitrogen, USA) IgG. The immunostained cut surface was counterstained with TO-PRO3 (Invitrogen, USA) to visualize the nuclei. The fluorescence-labeled cut surface was imaged with the Leica DM 5000 microscope (Leica Microsystems, Germany) or a confocal microscope (LSM510; Carl Zeiss, Germany) and analyzed with the Zen software.

Example 6

Flow Cytometry

After separating the hMSSCs of Examples 2.1 and 2.2 into a single cell suspension by treating with trypsin/EDTA and blocking nonspecific binding with 2% BSA in PBS, the cells were reacted with monoclonal antibodies against Sca, CD2, CD3, CD4, CD7, CD8, CD10, CD11b, CD14, CD19, CD20, CD31, CD34, CD44, CD45, CD51, CD56, CD73, CD90, CD105, CD146, CD166, CD235a and CD271 (BD Biosciences, USA) in a buffer solution [1× PBS, 1% BSA and 0.01% sodium azide] and then washed. The cells were reacted with Alexa Fluor 488 secondary mouse-IgGs (Invitrogen, USA), washed and then analyzed using a flow cytometer (FACStar Plus Flowcytometer, BD Biosciences, USA). Normal mouse IgGs (BD Biosciences, USA) were used as negative control group.

Example 7.1

Differentiation of Human Mesenchymal Stem Cell (hMSC) and hMSSC into Osteoblast In Vitro In order to differentiate the hMSSCs of Examples 2.1 and 2.2 into osteoblasts, the cells were cultured in an osteogenic differentiation medium (StemPro® osteogenic differentiation kit, Life Technologies, USA) under the condition of 37° C. and 5% $CO_2$ for 14 days. Alkaline phosphatase (Roche, Switzerland) staining and alizarin red S (Sigma, USA) staining were conducted to observe osteogenesis. The differentiation of hMSCs (Lonza, Switzerland) into osteoblasts was also compared in the same manner.

Example 7.2

Differentiation of Human Mesenchymal Stem Cell (hMSC) and hMSSC into Adipocyte In Vitro In order to differentiate the hMSSCs of Examples 2.1 and 2.2 into adipocytes, the cells were cultured in an adipogenic differentiation medium (StemPro® adipogenic differentiation kit, Life Technologies, USA) under the condition of 37° C. and 5% $CO_2$ for 14 days. Oil red O (Sigma, USA) staining was conducted to observe adipogenesis. The differentiation of hMSCs (Lonza, Switzerland) into adipocytes was also compared in the same manner.

Example 7.3

Differentiation of Human Mesenchymal Stem Cell (hMSC) and hMSSC into Cartilage Cell In Vitro In order to differentiate the hMSSCs of Examples 2.1 and 2.2 into cartilage cells, the cells were resuspended in a chondrogenic differentiation medium (StemPro® chondrogenic differentiation kit, Life Technologies, USA) and then centrifuged. For formation of micromass, the formed pellets were resuspended in a differentiation medium to $1 \times 10^5 / \mu L$ and then 5 µL of the cell solution was dropped at the center of a 96-well plate. After incubating the micromass for 2 hours under a high-humidity condition and adding a heated chondrogenic differentiation medium, incubation was performed in an incubator under the condition of 5% $CO_2$ and 37° C. The culture medium was re-feeded with 3- to 4-day intervals. 14 days later, the chondrogenic pellets were stained with Alcian blue. The differentiation of hMSCs (Lonza, Switzerland) into cartilage cells was also compared in the same manner.

Example 8.1

Differentiation Capacity of hMSSC into Endothelial Cell In Vitro

It was investigated whether the hMSSCs of Example 2.1 are differentiated into endothelial cells (ECs). The hMSSCs were differentiated by culturing with a medium for inducing differentiation into an EC (endothelial growth medium (EGM)-2 (Lonza, Walkersville, Md., USA) supplemented with 50 ng/mL VEGF (vascular endothelial growth factor: ProSpec, Rehovot, Israel) and 10 ng/mL bFGF (basic fibroblast growth factor; ProSpec, Rehovot, Israel) for 6 days. The differentiation was confirmed by immunocytochemistry.

Example 8.2

Differentiation Capacity of hMSSC into Skeletal Muscle Cell In Vitro

It was investigated whether the hMSSCs of Examples 2.1 and 2.2 are differentiated into skeletal muscle cells. The hMSSCs were differentiated by culturing with a skeletal muscle differentiation medium (DMEM supplemented with 2% B27) for 2 weeks on a Matrigel-coated cover slip. The differentiation was confirmed by immunocytochemistry.

Example 9

Induction of Differentiation from hMSSC to Nerve Cell In Vitro

For differentiation into nerve cells, the hMSSCs of Example 2.1 were plated on a polyornithine- and laminin-coated culture dish. 2 days later, the culture medium was exchanged with a medium for inducing differentiation into a nerve (Neurobasal medium containing 2% B27, 2 mM GlutaMAX and antibiotics). From day 7, 0.5 mM dibutyl cAMP (Sigma, USA) was added every day for 3 days. As a control group, human neural stem cells differentiated from H9 hESCs (Gibco, USA) were differentiated into nerve cells in the same manner. The differentiation was confirmed by immunocytochemistry.

Example 10.1

Differentiation Capacity of hMSSC in Mouse Kidney

In order to measure the differentiation capacity of the hMSSCs of Example 2.1 in mouse kidney, the hMSSCs were cultured with a MSCGM-CD (Lonza, Switzerland) medium for 2-5 passages and the hMSSCs ($2 \times 10^5$ cells) were cultured in an agarose gel well with DMEM+20% FBS for 2 days to form cell aggregates, which were transplanted into the kidney capsule of Balb/c nude mouse. Immunohistochemistry and immunohistochemical staining were performed 4 weeks after the transplantation.

Example 10.2

Differentiation Capacity of hMSSC in Mouse Hypoderm

In order to measure the differentiation capacity of the hMSSCs of Example 2.1 in mouse hypoderm, the hMSSCs were cultured with a MSCGM-CD (Lonza, Switzerland) medium for 2-5 passages and the hMSSCs ($2 \times 10^5$ cells) were loaded in fibrin glue (Greenplast®, Green Cross, Korea) to which 1 μg/mL hyaluronic acid (Sigma, USA) was added and then transplanted into the hypoderm of Balb/c nude mouse. Immunohistochemistry and immunohistochemical staining were performed 4 weeks after the transplantation.

Example 11.1

Osteogenesis Test Using hMSC

For analysis of osteogenesis of hMSCs in a thighbone fracture model, hMSCs (Lonza, Switzerland) were cultured with a MSCGM-CD (Lonza, Switzerland) medium for 7 passages and then absorbed into a collagen membrane (SK Bioland, Korea) cut to a size of 1 mm×1 mm. After perforating one tibia of a 6-week-old Balb/c nude mouse about 1 mm using a drill (Bosch Professional, Germany), the hMSCs absorbed in the collagen membrane were inserted into the fracture site of the mouse. Every two weeks, the mouse was anesthetized and micro-CT (Skyscan 1076, Antwerp, Belgium) images were obtained for the fracture site. Immunohistochemistry and immunohistochemical staining were performed 6 weeks later.

Example 11.2

Osteogenesis Test Using hMSSC

For analysis of osteogenesis of hMSSC in a thighbone fracture model, the hMSSCs of Example 2.1 were cultured with a MSCGM-CD (Lonza, Switzerland) medium for 2-5 passages and then absorbed into a collagen membrane (SK Bioland, Korea) cut to a size of 1 mm×1 mm. After perforating one tibia of a 6-week-old Balb/c nude mouse about 1 mm using a drill (Bosch Professional, Germany), the hMSSCs absorbed in the collagen membrane were inserted into the fracture site of the mouse. Every two weeks, the mouse was anesthetized and micro-CT (Skyscan 1076, Antwerp, Belgium) images were obtained for the fracture site. Immunohistochemistry and immunohistochemical staining were performed 6 weeks later.

Example 12

Micro-CT

The bone formed in the kidney into which the hMSSCs were transplanted in Example 10.1 was scanned by micro-CT (Skyscan 1076, Antwerp, Belgium) to obtain 3D CT (computed tomography) images. Then, the data were digitalized with a frame grabber and the resulting images were transmitted to a computer using the Comprehensive TeX Archive Network (CTAN) topographic reconstruction software.

Example 13

Measurement of scx, Runx2 and MYH9 mRNA Expression Levels

RNAs were extracted from the transplant of the hMSSCs of Example 2.1 in the kidney using 500 μL of Trizol (Life Technologies, USA) according to the manufacturer's protocol. After treating the transplant of the hMSSCs in the kidney with DNAse (RQ1 DNase, Promega, USA), 500 ng of RNAs were reversely transcribed to cDNAs using oligo-d(T) and random hexamers according to the Superscript III RT (Life Technologies, USA) first-strand cDNA synthesis protocol. qRT-PCR was conducted on the StepOne Plus PCR cycler (Applied Biosystems) using SYBR green (Applied Biosystems, Foster City, Calif.). mRNA expression data were analyzed using the ΔΔCT method and normalized with glyceraldehyde-3-phosphate dehydrogenase (GAPDH) for gene detection. The primers necessary for the qRT-PCR were purchased from Qiagen (USA). As a control group, RNAs were extracted from hMSSCs and qRT-PCR was conducted in the same manner.

Experimental Results

Test Example 1

Confirmation of Induction of Differentiation of hMSSC Derived from hESC

Aging Marker

The differentiation from hESCs to hMSSCs was induced as described in Example 2 and the morphological change of the induced hMSSCs was observed. The result is shown in FIG. 1A. As seen from FIG. 1A, it was confirmed that the undifferentiated single H9 hESCs were differentiated into cells with fibroblast morphology within 7 passages. They grew with similar morphologies for 10 passages or longer, from passage 7 to passage 17, and showed a positive response to staining with the aging marker β-galactosidase since passage 19, suggesting that aging was progressed.

Confirmation of Pluripotency Marker by Immunofluorescence Method

Figure 1B:
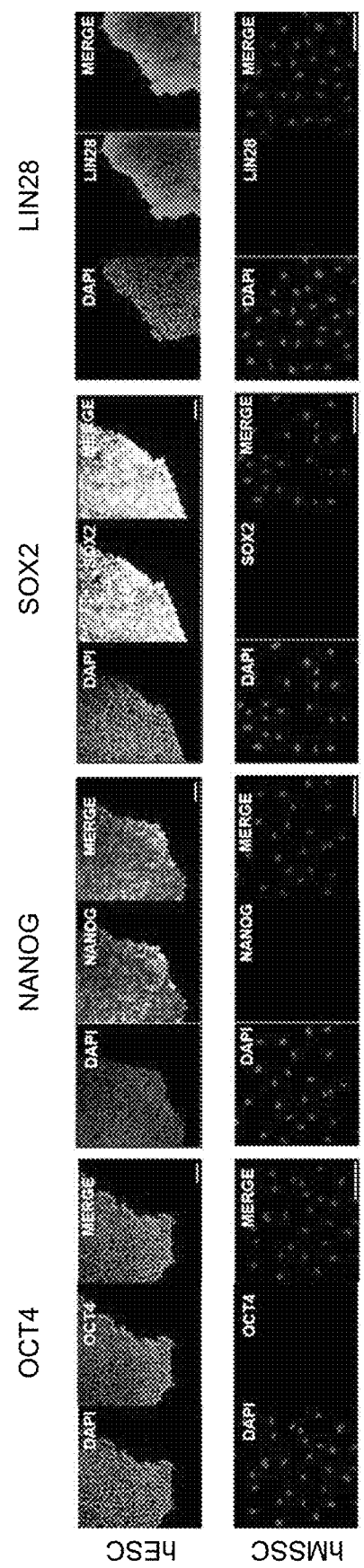

The expression of pluripotency markers in the hMSSCs after 7 passages or longer since the induction from the hESCs was observed by the immunofluorescence method. The result is shown in FIG. 1B. For comparison, the expression of pluripotency markers in H9 hESCs was investigated by the immunofluorescence method.

As seen from FIG. 1B, the H9 hESCs were positive for all of OCT4, NANOG, SOX2 and LIN28, suggesting that they have pluripotency. In contrast, the hMSSCs induced from the H9 hESCs were negative for OCT4, NANOG, SOX2 and LIN28.

Figure 1C:
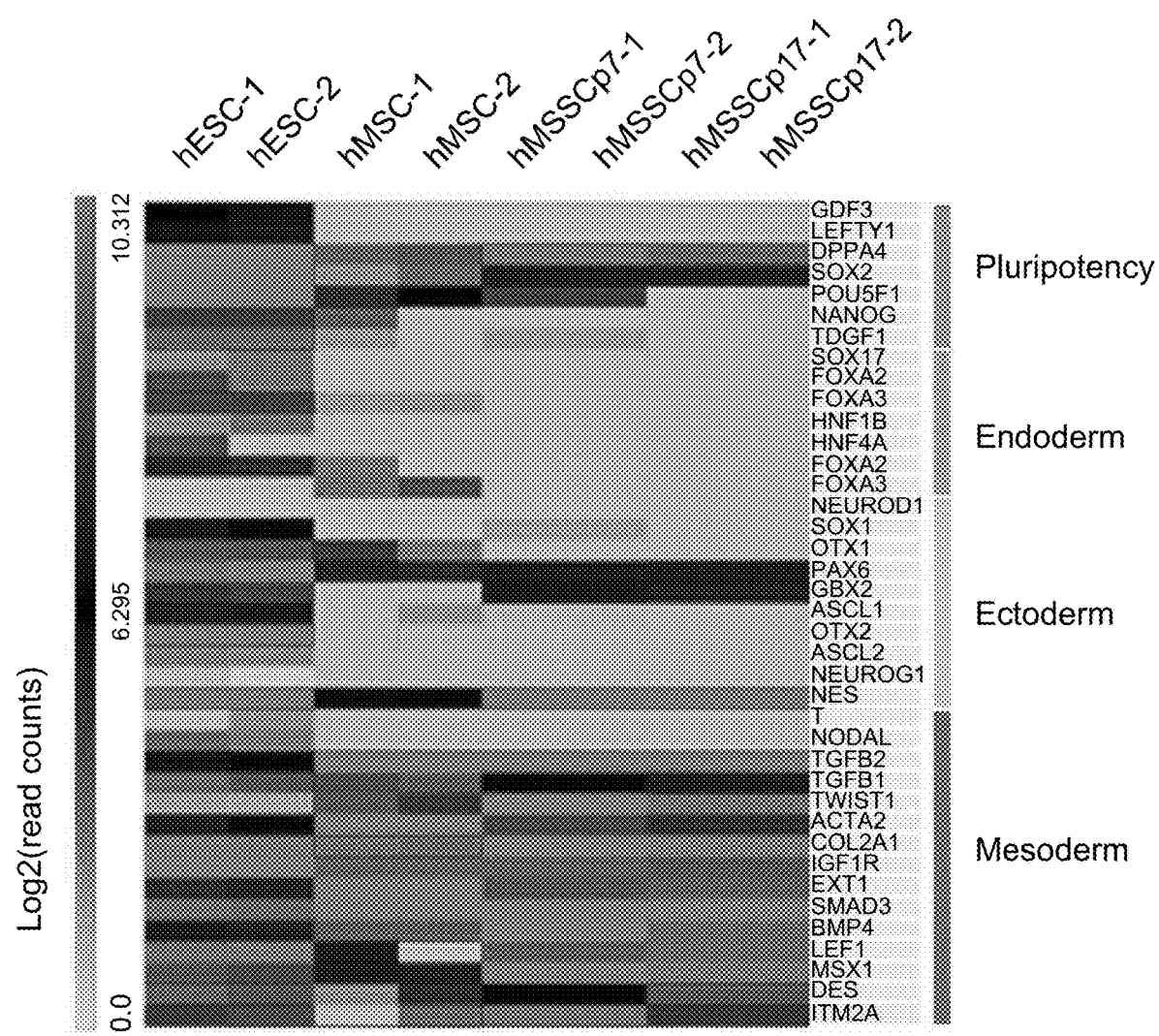

Confirmation of Pluripotency, Ectodermal, Mesodermal and Endodermal Markers Through RNA Sequencing The expression of pluripotency, ectodermal, mesodermal and endodermal markers in hESCs, hMSCs and hMSSCs at passages 7 and 17 was investigated through RNA sequencing. The result is shown in FIG. 1C. The expression of the mRNAs of the pluripotency markers TDGF, NANOG, POU5F1, SOX2, DPPA4, LEFTY1, GDF3, etc. was confirmed in the H9 hESCs (hESC-1, hESC-2). In contrast, for the hMSSCs induced from the H9 hESCs, the expression of the pluripotency marker DPPA4 was observed but the expression of the pluripotency markers TDGF, NANOG, POU5F1, LEFTY1 and GDF3 was not observed. The expression level of DPPA4 was comparable to that in the H9 hESCs.

The expression of DPPA4 was not observed in the human mesenchymal stem cells. In addition, the hMSSCs were positive for the ectodermal marker NES, were positive for most mesodermal markers except for DES and the early mesodermal markers T and nodal and were negative for most endodermal markers. In particular, NES was not expressed in the mesenchymal stem cells.

Figure 1D:
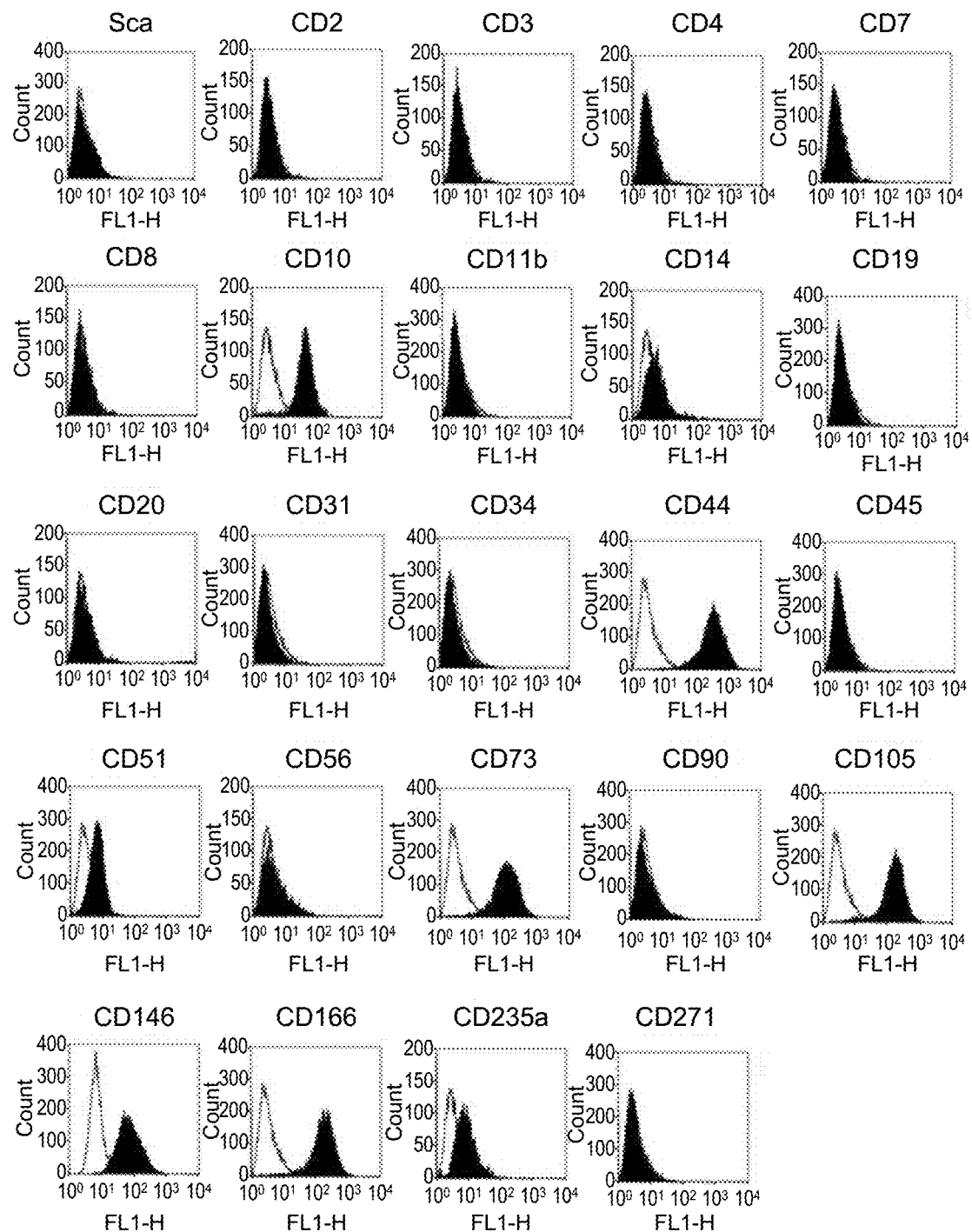
Figure 1E:
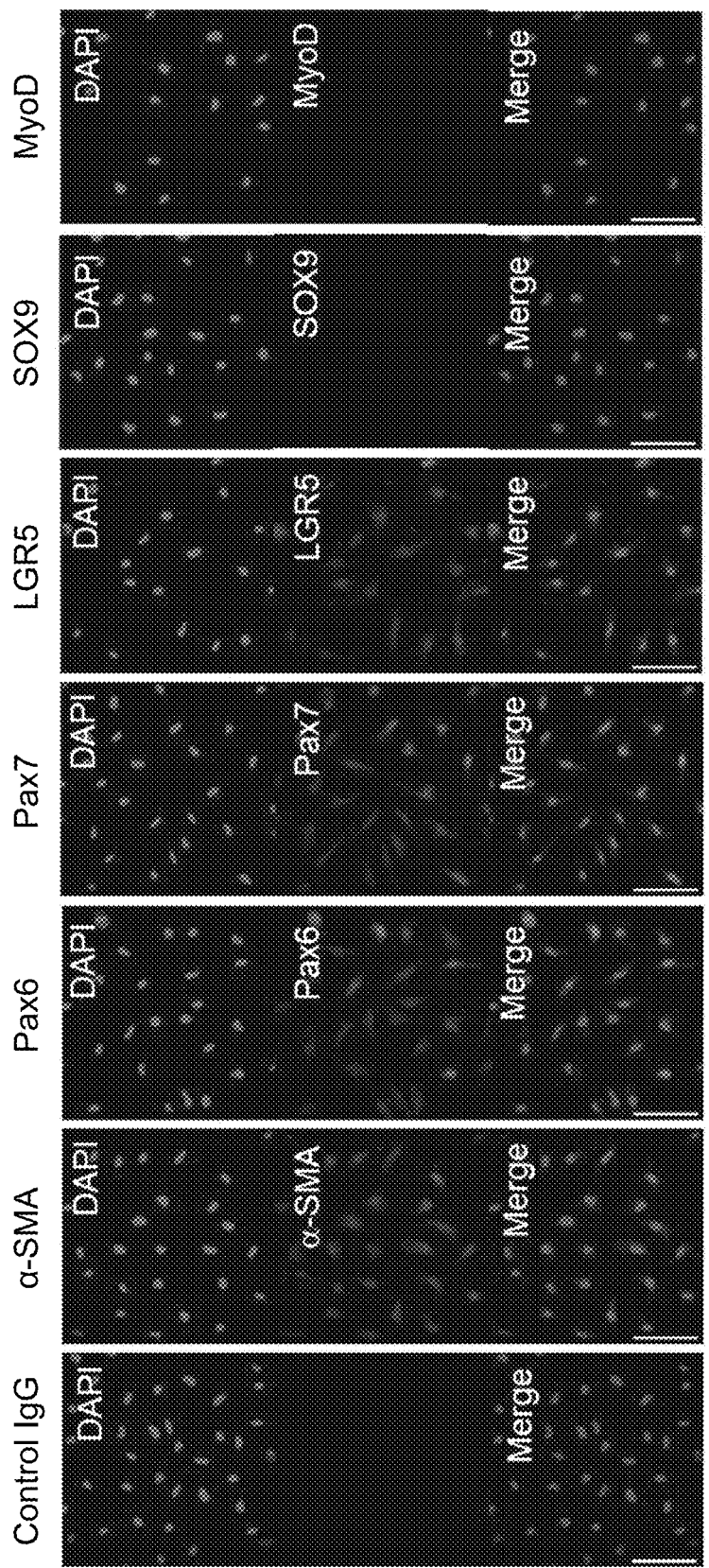

Confirmation of Mesenchymal Stem Cell Markers Through Expression of Cell Surface Antigens The expression of antigens on the surface of hMSSCs was measured as seen from FIG. 1D. When the expression of mesenchymal stem cell-specific cell surface antigens was investigated, the expression of the mesenchymal stem cell markers CD44, CD51, CD73, CD105, CD146 and CD166 was observed in the hMSSCs but the expression of the mesenchymal stem cell markers CD90 and CD271 was not observed. In addition, the expression of the vascular cell surface markers CD2, CD3, CD7, CD8, CD11 b, CD14, CD19, CD20, CD31, CD34 and CD56 was not observed but the expression of the pre-B cell marker CD10 was observed.

Confirmation of Other Cell-Specific Markers

The expression of various tissue-specific markers was analyzed to investigate the characteristics of hMSSCs as shown in FIG. 1F. The mesodermal marker alpha smooth muscle actin (a-SMA), the neuroectodermal marker Pax6, the myogenic satellite marker Pax7, the intestinal stem cell marker LGR5, etc. were expressed, whereas the chondrocyte marker SOX9, the myoblast marker MyoD, etc. were not expressed. This suggests that the hMSSCs are progenitor cells prior to differentiation into cartilage cells and muscle cells.

Test Example 2

Differentiation Capacity of hMSSC In Vitro

Figure 2A:
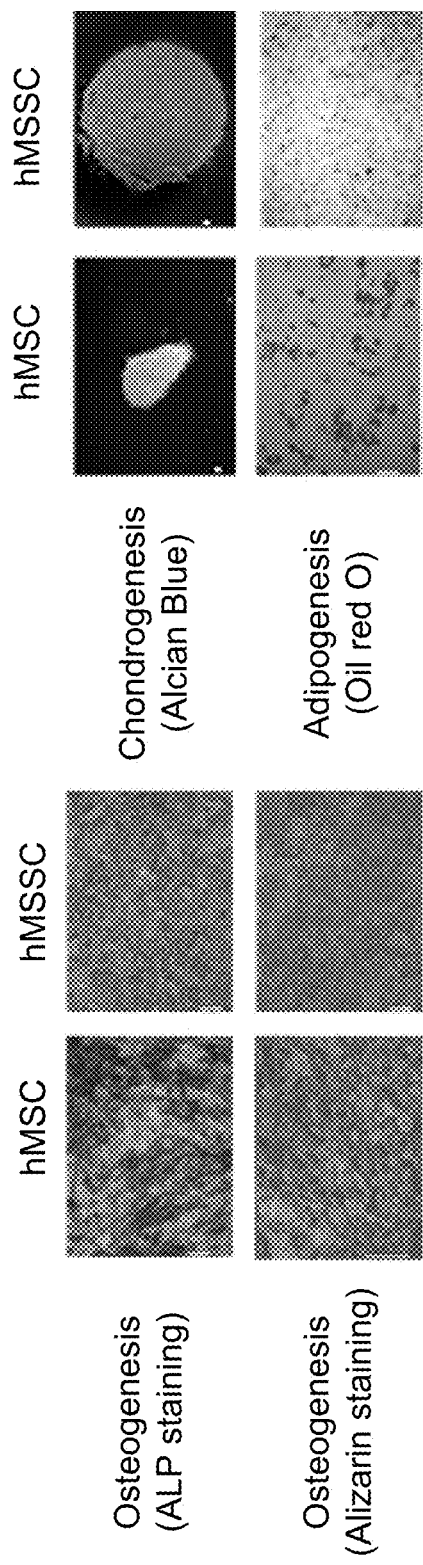
FIGS. 2A-2E show a result of comparing the in-vitro differentiation capacity of hMSSC with other types of cells.

In-vitro osteogenesis, chondrogenesis and adipogenesis were tested for hMSCs and the hMSSCs of Example 2.1 (Example 7) and the result is shown in FIG. 2A. From FIG. 2A, it was confirmed that the hMSCs could be differentiated into bone, cartilage and fat in vitro. Meanwhile, the hMSSCs were differentiated into bone and cartilage but were hardly differentiated into fat under the same conditions in vitro. That is to say, the cells were found to be functionally different from the mesenchymal stem cells.

Differentiability into Skeletal Muscle

It was investigated whether the hMSSCs of Test Example 1 has the potential to be differentiate into skeletal muscle.

Figure 2B:
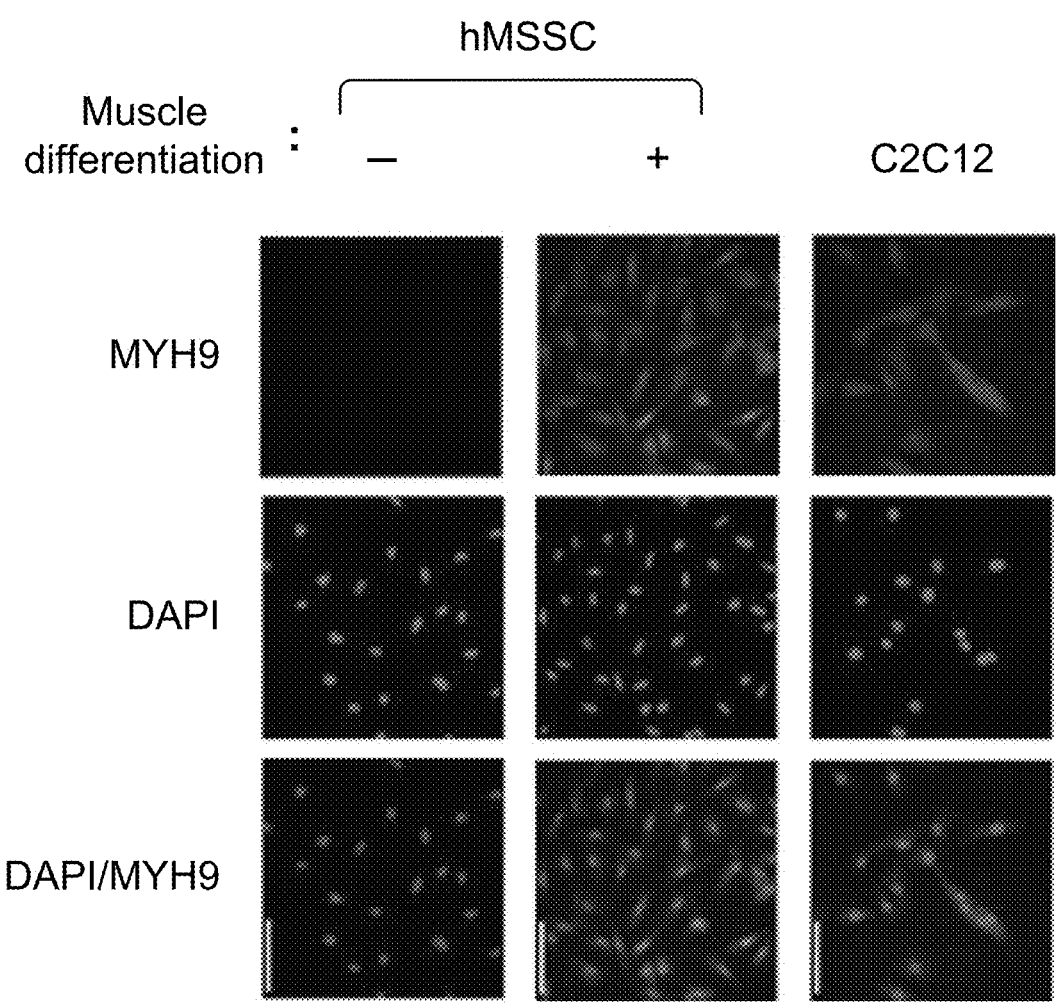

The hMSSCs were cultured for 2 weeks in a medium for inducing differentiation into skeletal muscle (DMEM containing 2% B27) on a Matrigel-coated cover slip and then immunofluorescence assay was performed for the skeletal muscle marker MYH9. The result is shown in FIG. 2B. C2C12 cells were used as a control group. As seen from FIG. 2B, it was confirmed that the skeletal muscle-specific marker MYH9 was expressed when the hMSSCs were cultured in the skeletal muscle differentiation medium, suggesting that the hMSSCs have the potential to be differentiate into skeletal muscle.

Differentiability into Endothelial Cell

It was investigated whether the hMSSCs of Test Example 1 has the potential to be differentiate into endothelial cells.

Figure 2C:
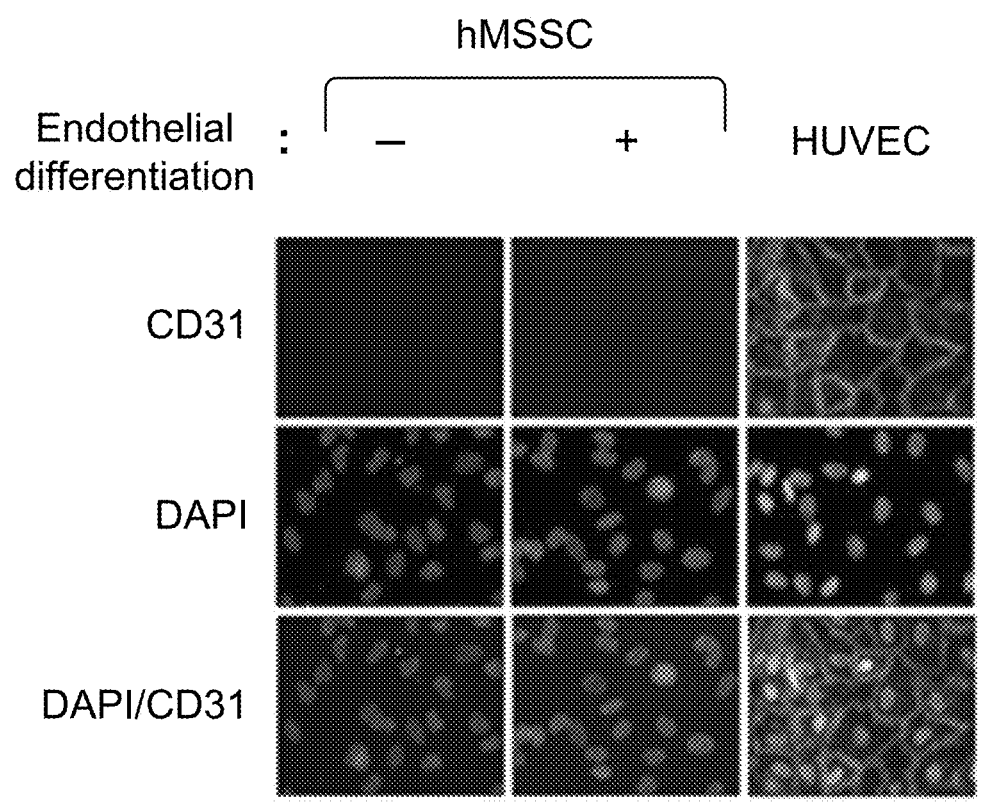
Figure 2D:
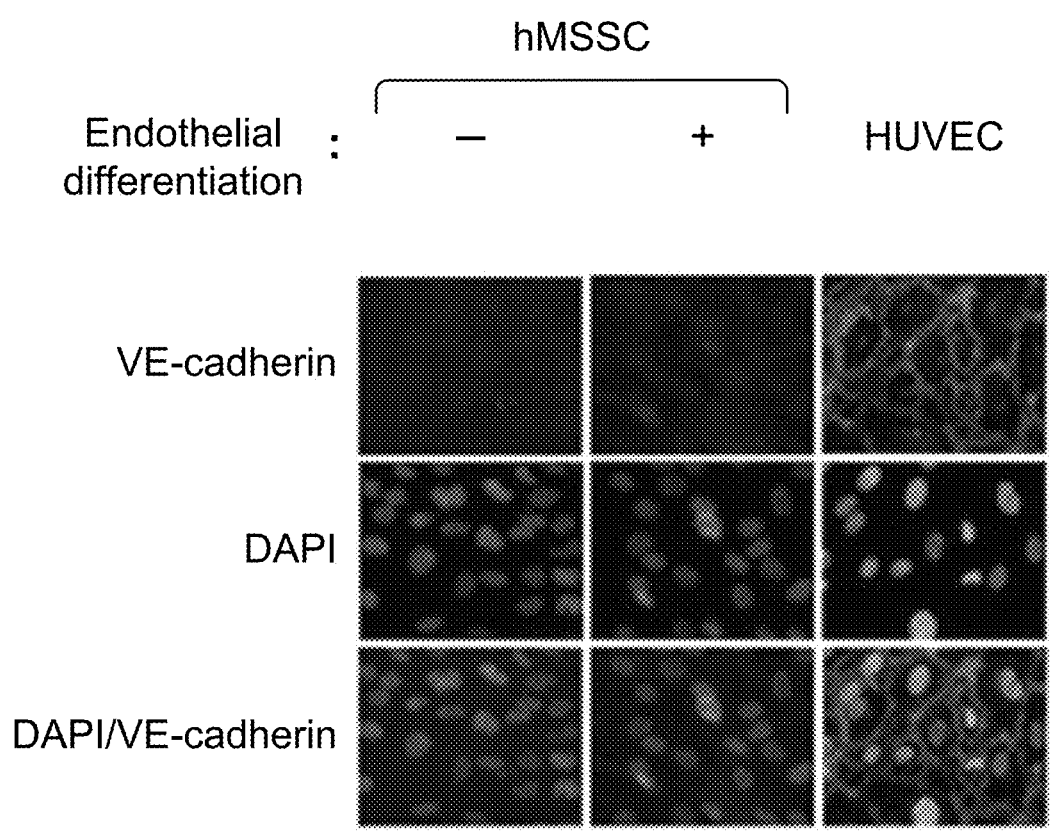

The hMSSCs were cultured for 6 days in a medium for inducing differentiation into an EC (endothelial growth medium (EGM)-2 (Lonza, Walkersville, Md.)) supplemented with 50 ng/mL VEGF (vascular endothelial growth factor: ProSpec, Rehovot, Israel) and 10 ng/mL bFGF (basic fibroblast growth factor; ProSpec) and then immunofluorescence assay was performed for the endothelial cell markers CD31 and VE-cadherin. The result is shown in FIGS. 2C and 2D. HUVECs were used as a positive control group for endothelial cell differentiation. As seen from FIG. 2C and FIG. 2D, the expression of CD31 and VE-cadherin was not observed in the hMSSCs, suggesting that the hMSSCs lack the potential to be differentiate into endothelial cells. In contrast, expression of the markers were observed in the control group HUVECs.

Differentiability into Nerve Cell

Figure 2E:
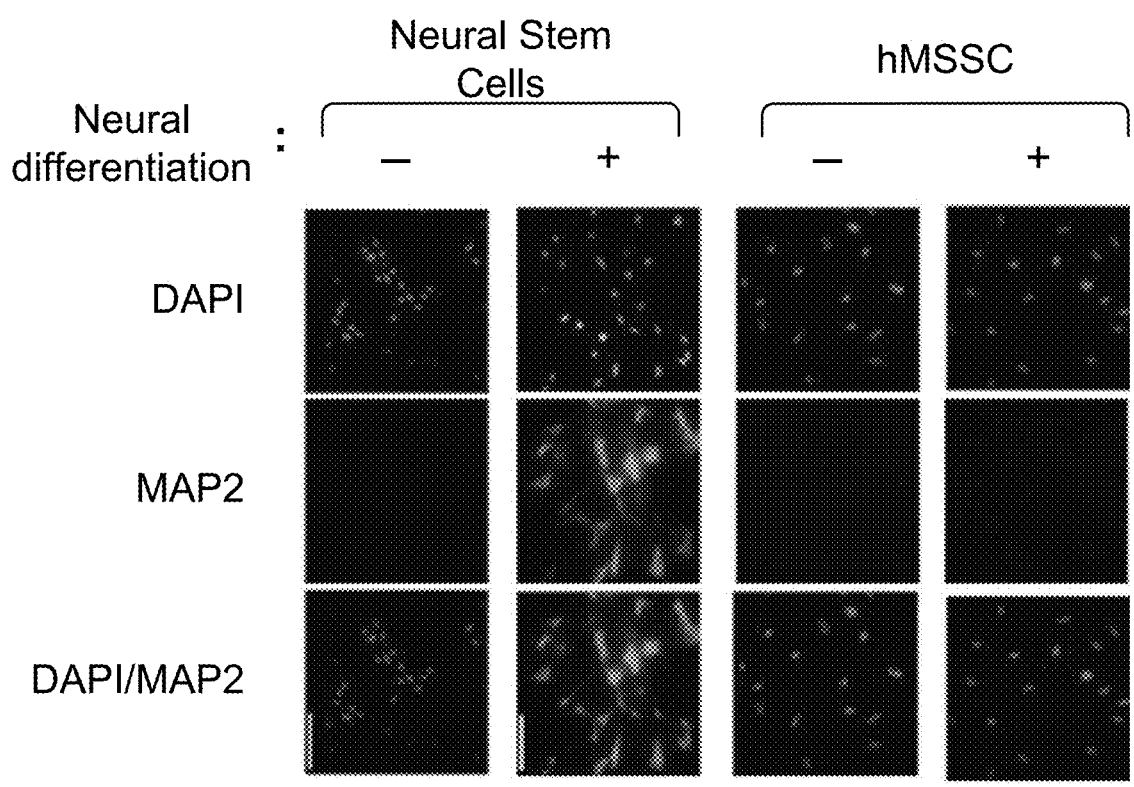

The hMSSCs were incubated for 7 days in a medium for inducing differentiation into a nerve (Neurobasal medium containing 2% B27, 2 mM GlutaMAX and antibiotics) and then cultured for 3 days while adding 0.5 mM dibutyl cAMP (Sigma) every day. Then, immunofluorescence assay was performed for the nerve cell differentiation marker MAP2. The result is shown in FIG. 2E. NSCs (neuronal stem cells) were used as a positive control group for nerve cell differentiation. As seen from FIG. 2E, the cell morphology of the NSCs was changed to that of nerve cells and the expression of the nerve cell-specific marker MAP2 was observed, suggesting that the cells were differentiated into nerve cells. In contrast, the hMSSCs showed no change in cell morphology and the expression of MAP2 was not observed, suggesting that they lack the potential to be differentiate into nerve cells.

Although the hMSSCs were positive for the ectodermal marker NES as confirmed in Test Example 1, they were not differentiated into nerve cells. It was confirmed that the hMSSC can be differentiated into the mesoderm, more particularly to bone, cartilage and muscle.

Test Example 3

Confirmation of Differentiation of hMSSC into Bone, Cartilage, Muscle, Fat and Tendon In Vivo In order to measure the differentiability of the hMSSCs induced in the same manner as in Example 2 in vivo, the hMSSCs were transplanted into the kidney (Example 10.1) and hypoderm (Example 10.2) of an immune-deficient mouse. After transplanting the hMSSCs into mouse kidney and staining tissues with H&E 3-4 weeks later, immunofluorescence staining was performed for bone-, muscle-, fat- and tendon-specific markers and the cell nuclei were counterstained with TO-PRO3. The result is shown in FIG. 3A and FIG. 3B.

Figure 3A:
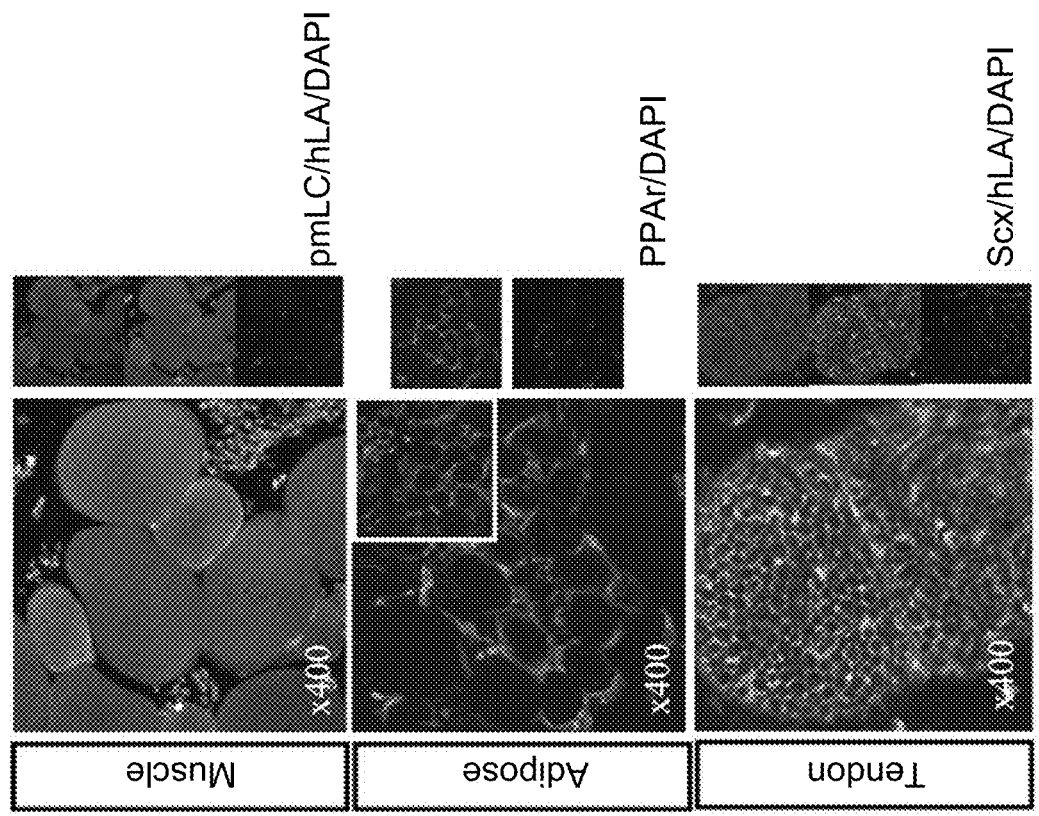
FIGS. 3A-3C show a result of measuring the differentiability of hMSSC in vivo.
Figure 3A:
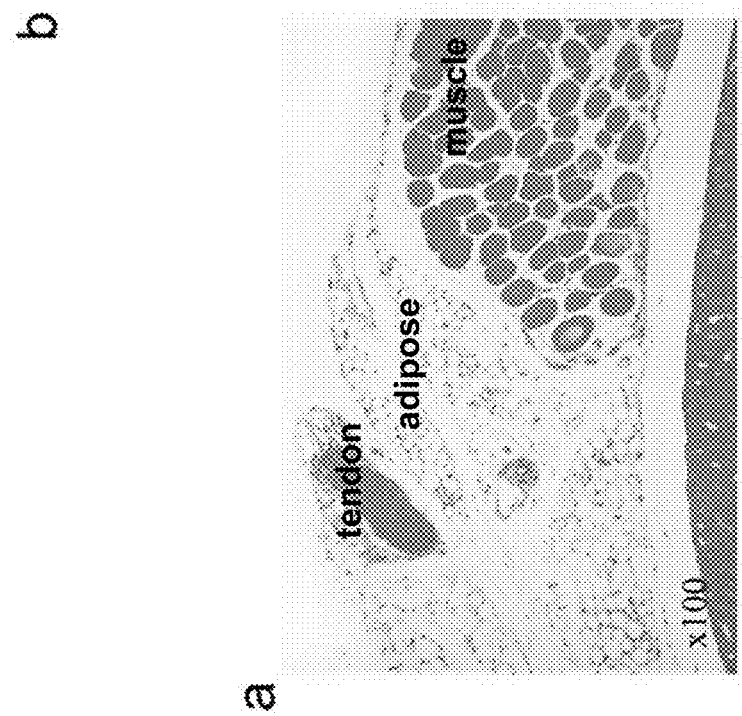

FIG. 3A shows images obtained 4 weeks after culturing the hMSSCs in a MSCGM-CD (Lonza, Switzerland) medium for 2-5 passages and transplanting them into the kidney. The H&E staining result shows that muscle, fat and tendon were formed well in the kidney (FIG. 3A-a). When the differentiated muscle tissues were analyzed, the differentiation into skeletal muscle was observed but the differentiation into smooth muscle was not observed. In contrast, when human MSCs were transplanted under the same condition, muscle, fat, tendon, etc. were not formed at all (data not shown). When immunohistochemical assay was performed, it was confirmed that each differentiated tissue was positive for the muscle marker phospho-myosin light chain (pMLC), the adipose marker PPARgamma (PPAr), the tendon marker sleraxis (Scx), etc. and was also positive for the human cell marker hLA (human leukocyte antigen). From this, it can be seen that transplanted hMSSCs were differentiated into muscle, fat and tendon cells (This is contrary to the in-vitro test result showing no differentiation into fat) (FIG. 3A-b).

Figure 3B:
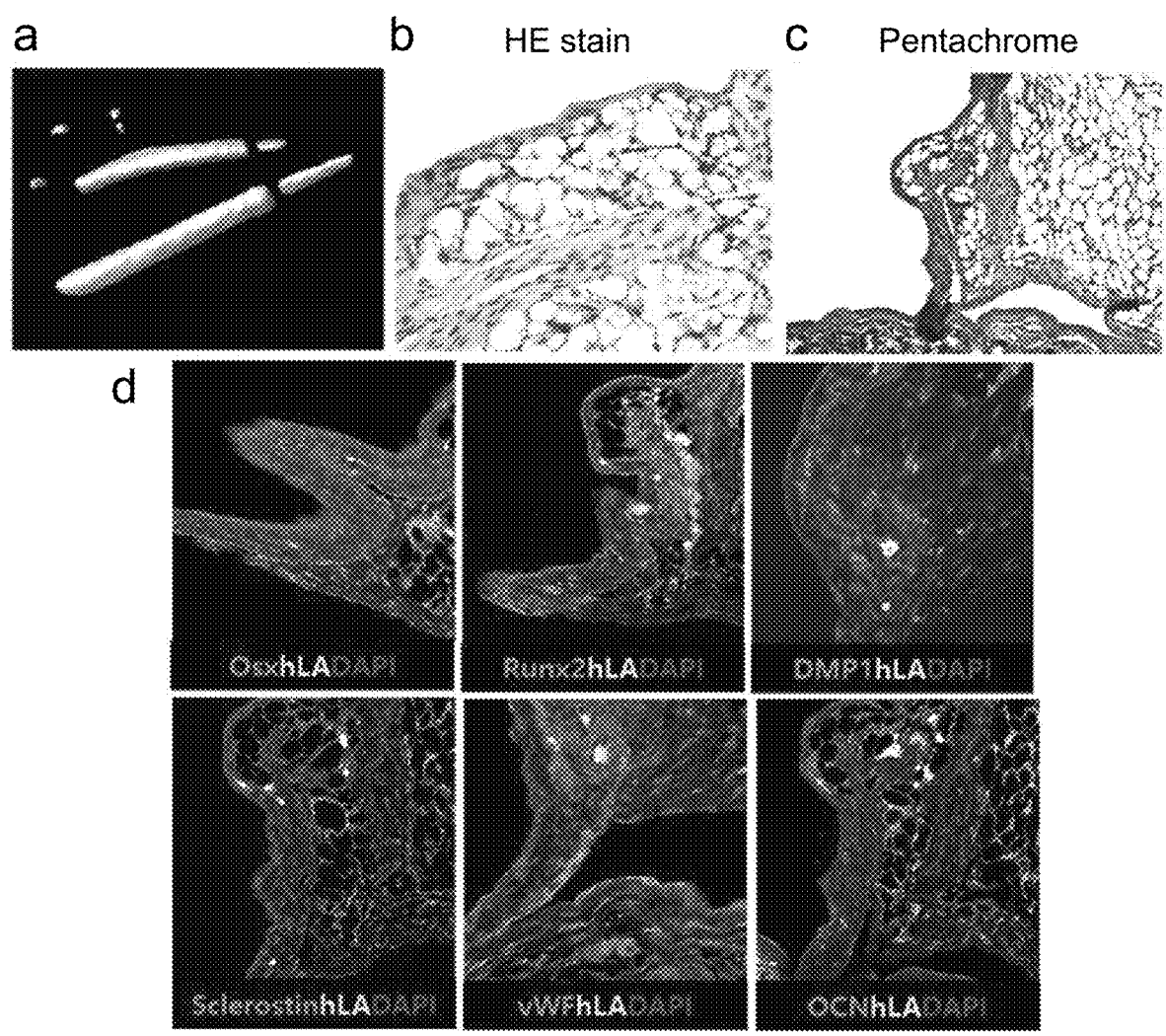

FIG. 3B-a shows a result of micro-CT scanning showing that hard tissue, or bone, was formed at the site where the hMSSC was transplanted into the kidney.

Figure 3C:
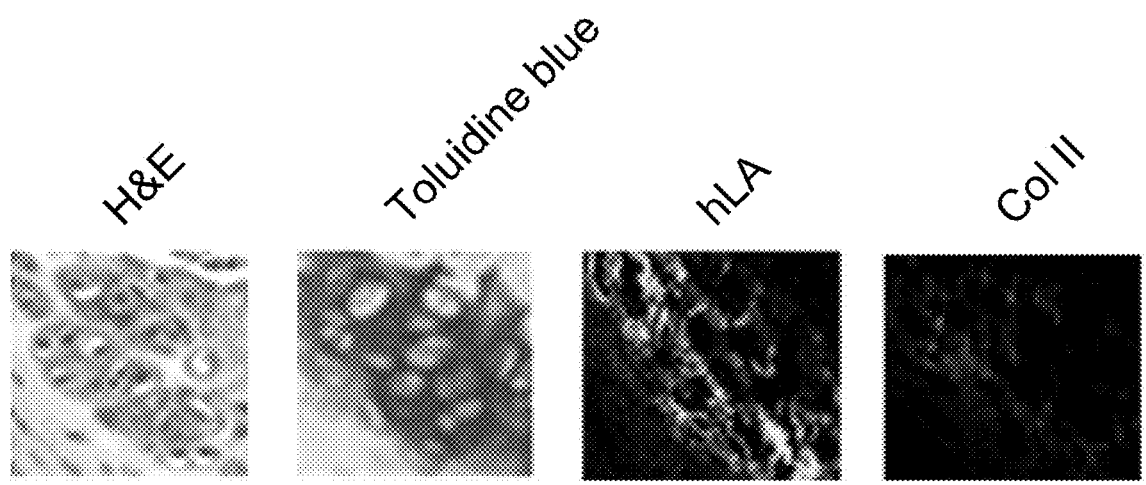

FIGS. 3B-b and 3B-c show a result of confirming bone formation by H&E and pentachrome staining. It can be seen that the transplanted hMSSCs were differentiated into bone in the kidney capsule.

FIG. 3B-d shows the immunohistochemical assay at the transplanted site. It was confirmed that the cells in the tissue were positive for the human cell marker hLA (human leukocyte antigen), the bone markers Osx (osterix), Runx2, DMP1, OCN (osteocalin), etc. and the vascular marker vWF, suggesting that bone was confirmed. Therefore, it can be seen that the transplanted hMSSCs were differentiated into bone.

FIG. 3C shows that the hMSSCs transplanted into mouse hypoderm by loading in fibrin glue to which hyaluronic acid was added were differentiated into cartilage cells. The cartilage formation was confirmed by H&E and toluidine blue staining.

Taken together, it was confirmed that the hMSSCs of the present disclosure can be differentiated into cartilage, muscle, tendon and bone at the transplanted site and have superior differentiation capacity.

Test Example 5

Confirmation of Fracture Recovery Effect of hMSSC

Figure 4A:
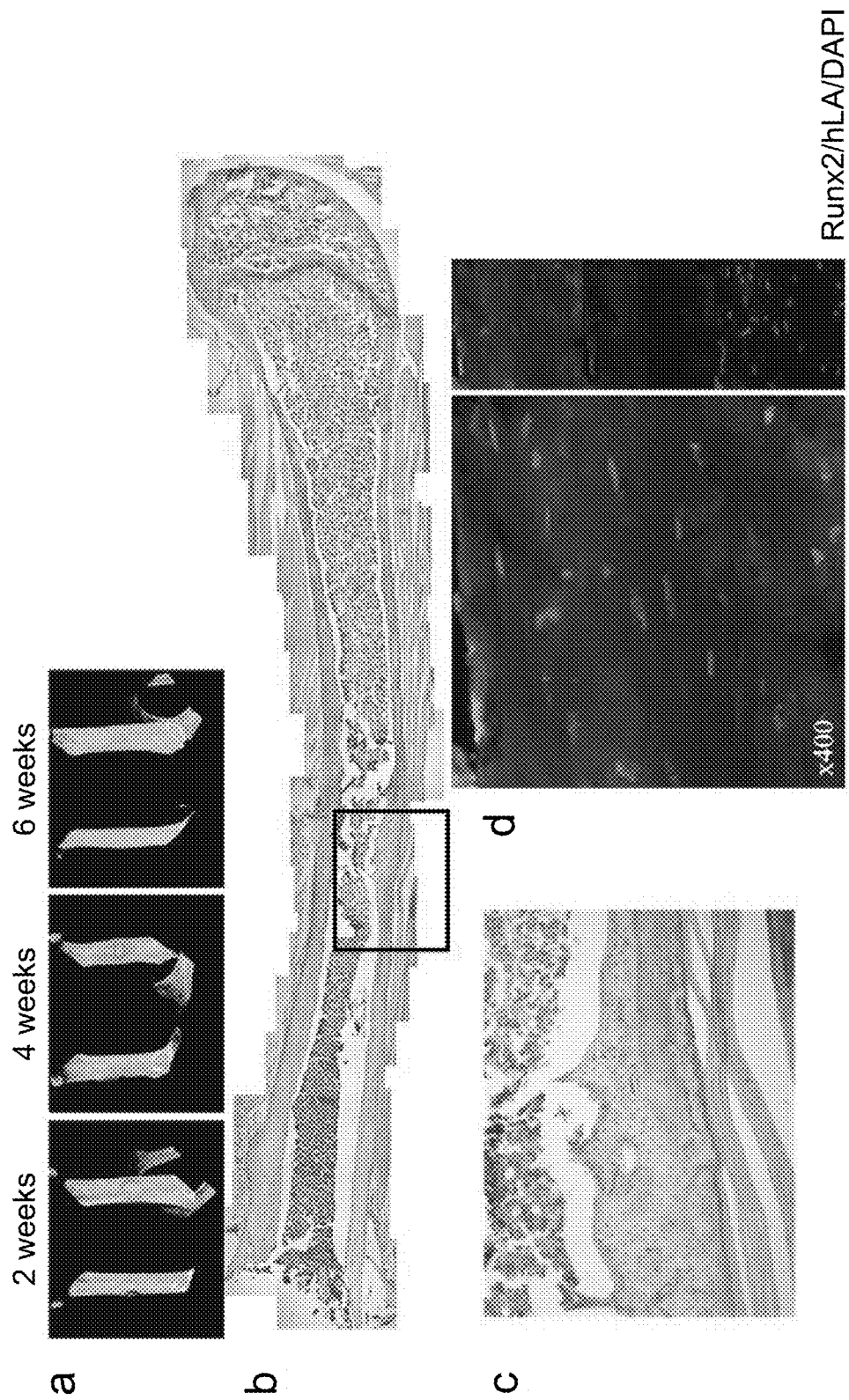
FIGS. 4A-4B show a result of confirming the effect of hMSSC on recovery of fracture.
Figure 4B:
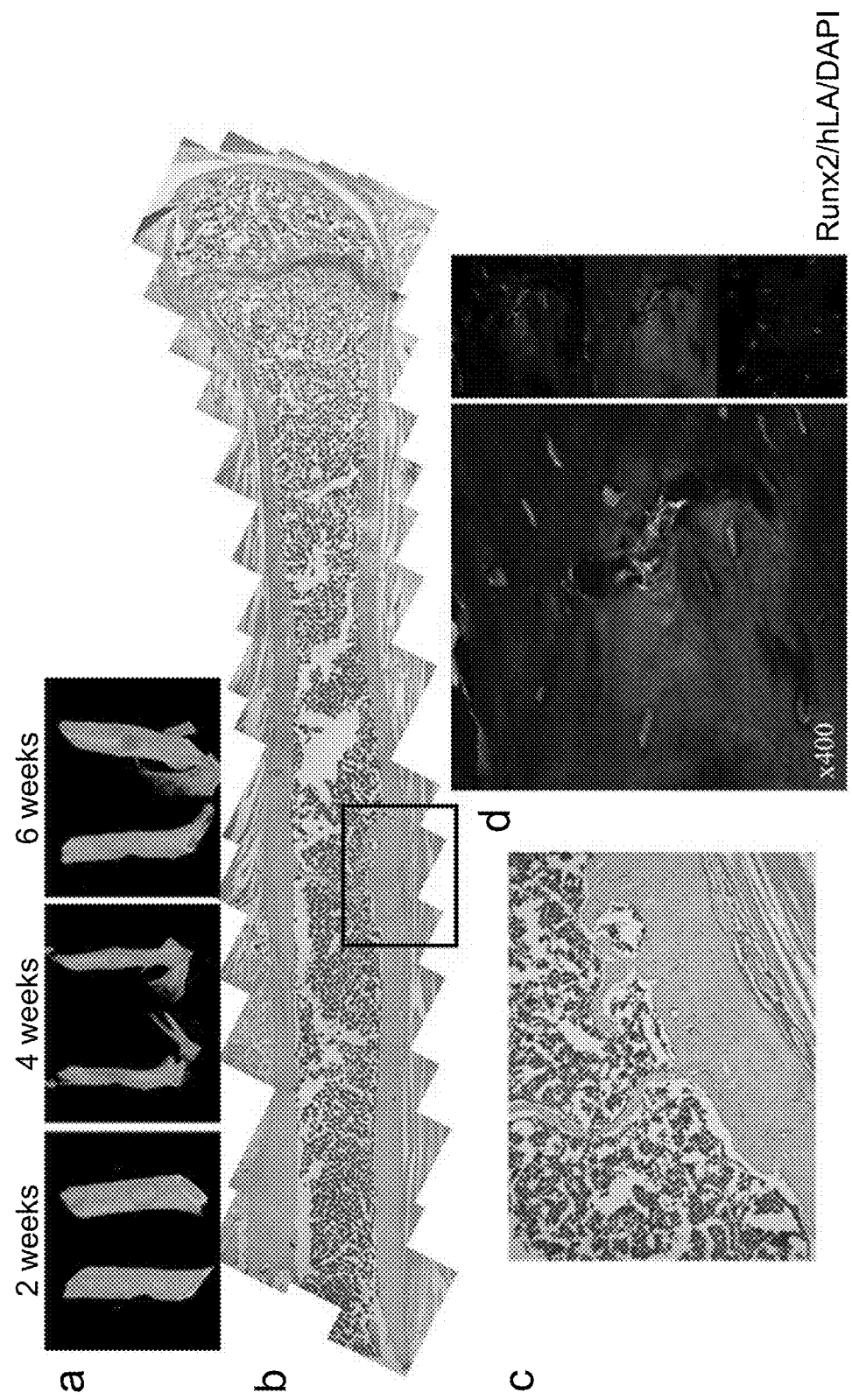

In order to confirm the fracture recovery of hMSSCs induced in the same manner as in Example 2, osteogenesis test was performed as in Example 11. The result is shown in FIGS. 4A-4B.

It was confirmed that, when the hMSCs were transplanted into a fracture site in a thighbone fracture model, bone was formed about 6 weeks later at the fracture site. However, because the osteogenic site was positive for the bone marker Runx2 but negative for the human cell marker hLA, it was estimated that the osteogenesis was not by the transplanted hMSCs but by the mouse cells (FIG. 4A). In contrast, when hMSSCs were transplanted under the same condition, bone was formed about 6 weeks later at the fracture site, with the osteogenic site being positive for Runx2 and positive for the human cell marker hLA. This suggests that the bone formation was owing to the differentiation of the hMSSCs (FIG. 4B).

Test Example 6

Induction of Differentiation from hiPSC into hMSSC and Characterization of Induced hiPSC hiPSCs (human induced pluripotent stem cells) were prepared by reprogramming embryonic IMR90 fibroblasts by overexpressing OCT4, KLF4, SOX2 and MYC using Sendai virus according to the method developed by Hasegawa et al. (Fusaki et al., 2009).

iPS-hMSSCs were obtained by inducing hMSSCs from hiPSCs in the same manner as in Example 2. The expression level of the pluripotency markers Oct4, Nanog, Sox2 and Lin28 in the iPS-hMSSCs was investigated by immunofluorescence assay and RT-PCR. The result is shown in FIG. 5A.

Figure 5A:
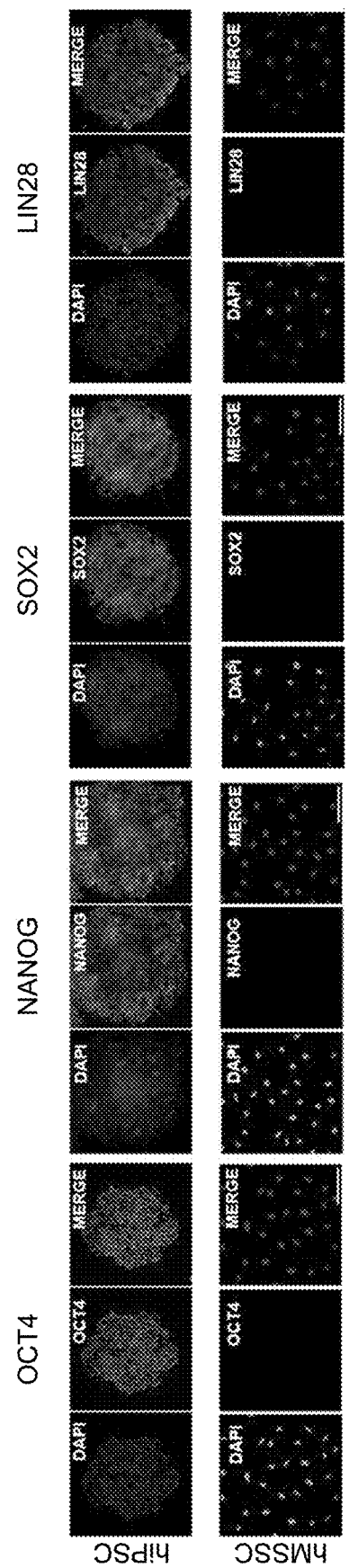
FIGS. 5A-5D show a result of investigating whether hiPSC is also differentiated into hMSSC like hESC.

As seen from FIG. 5A, iPS cells were positive for OCT4, NANOG, SOX2 and LIN28, suggesting that the cells have pluripotency. In contrast, the iPS-hMSSCs were negative for the pluripotency markers OCT4, NANOG, SOX2 and LIN28.

Figure 5B:
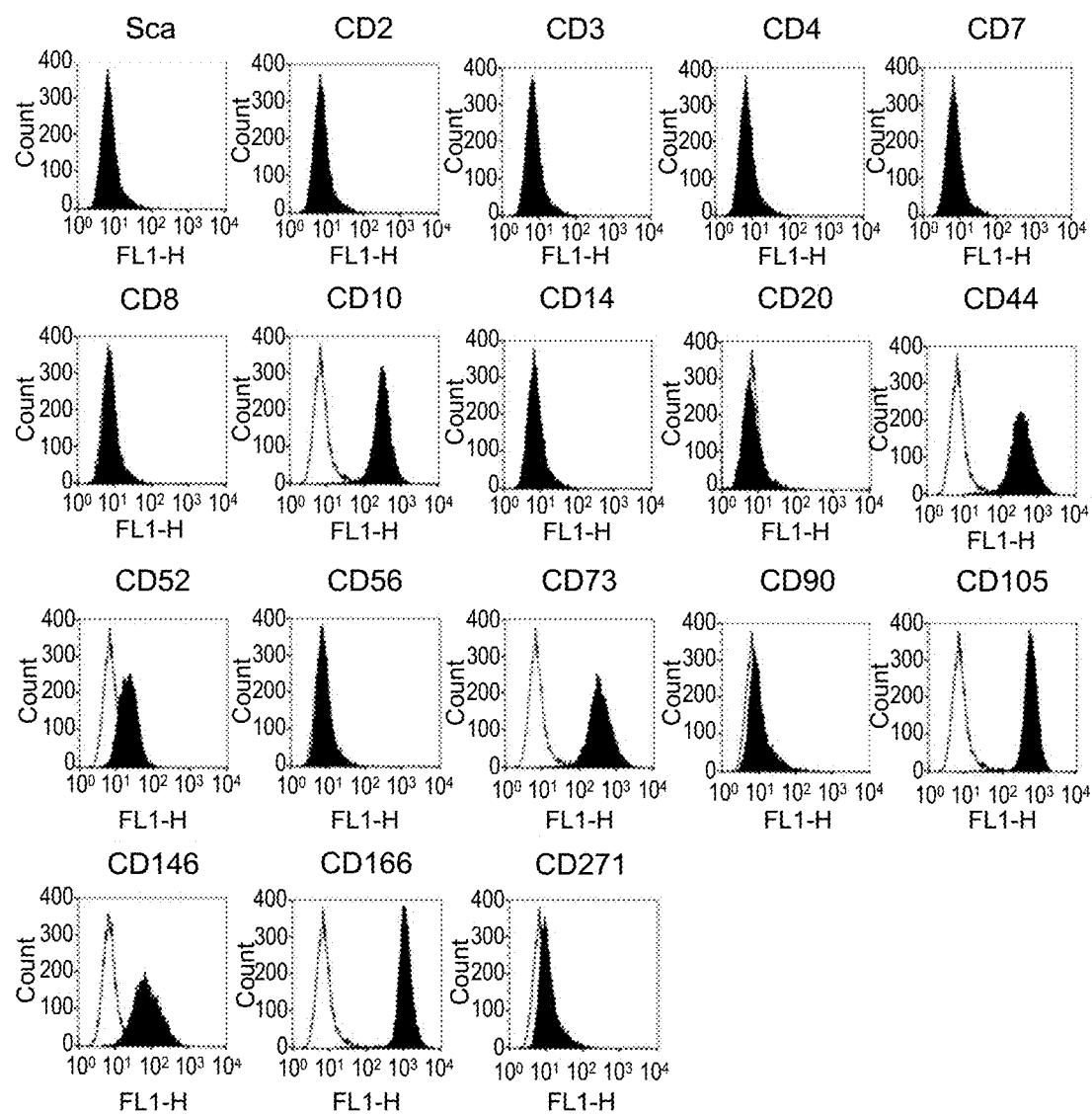

FIG. 5B shows a result of measuring the expression of surface antigens for the iPS-hMSSCs. When the expression of mesenchymal stem cell-specific cell surface antigens was investigated, it was confirmed that, among the mesenchymal stem cell markers, CD44, CD51, CD73, CD105, CD146 and CD166 were expressed in the iPS-hMSSCs, but CD90 and CD271 were not expressed in the iPS-hMSSCs. In addition, the pre-B cell marker CD10 was expressed whereas the vascular cell surface markers CD2, CD3, CD7, CD8, CD14, CD20 and CD56 were not expressed.

Figure 5C:
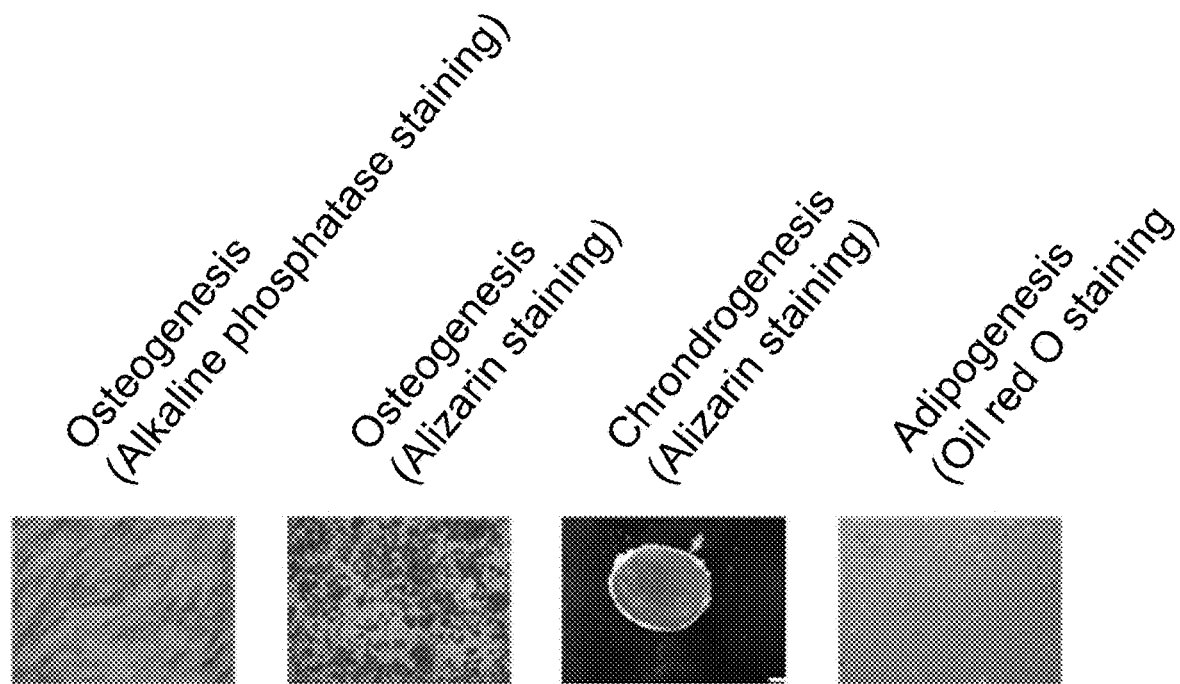

Also, the osteogenesis, chondrogenesis and adipogenesis of the iPS-hMSSCs were evaluated in the same manner as in Test Example 2. The result is shown in FIG. 5C. As seen from FIG. 5C, it was confirmed that the hMSSCs induced from the hiPSCs were differentiated into bone and cartilage in vitro but were hardly differentiated into fat.

Figure 5D:
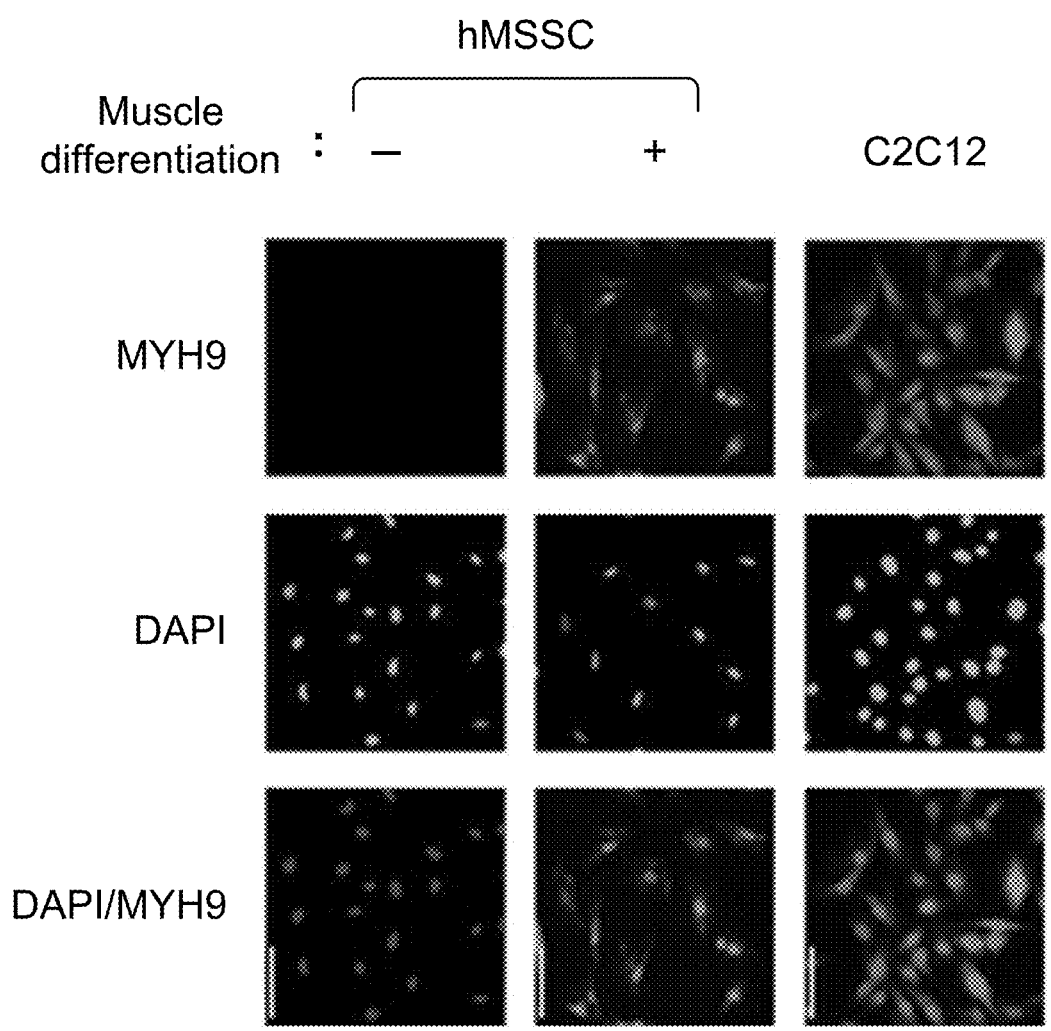

In addition, the iPS-hMSSCs were cultured for 2 weeks in a medium for inducing differentiation into skeletal muscle (DMEM containing 2% B27) on a Matrigel-coated cover slip and then immunofluorescence assay was performed for the skeletal muscle marker MYH9. The result is shown in FIG. 5D. C2C12 cells were used as a control group. As seen from FIG. 5D, it was confirmed that the hMSSCs induced from the hiPSCs have the potential to be differentiate into skeletal muscle.

Taken together, it was confirmed that the hMSSCs induced from the hiPSCs have the same characteristics as the hMSSCs induced from the hECSs, suggesting that hMSSCs can be obtained using hiPSCs instead of hECSs.

Test Example 7

Differentiability of hMSSC Induced from hiPSC In Vivo

Transplantation into Kidney

After transplanting the hMSSCs of Test Example 6 into mouse kidney, the tissue was stained with H&E 3-4 weeks later. It was confirmed that muscle, fat and tendon were formed in the kidney. The immunohistochemical assay result for the transplanted site was positive for the muscle marker phospho-myosin light chain (pMLC), the adipose marker PPARgamma (PPAr), the tendon marker sleraxis (Scx), etc. and also positive for the human cell marker hLA (human leukocyte antigen). Also, the result was positive for the bone markers Osx (osterix), Runx2, DMP1, OCN (osteocalin), etc. Through this, it was confirmed that the hMSSCs induced from the iPSCs can be differentiated into muscle, fat, tendon and bone.

Transplantation into Hypoderm

When the hMSSCs of Test Example 6 were transplanted into mouse hypoderm by loading in fibrin glue to which hyaluronic acid was added, it was confirmed through H&E and toluidine blue staining that the hMSSCs can be differentiated into cartilage.

Comparative Example 1

Comparison of Differentiation Capacity of Noggin-Containing MSSC Medium and Conditioned Medium-Containing CM Medium The differentiation capacity of a medium (hereinafter, "CM medium") obtained by replacing the human noggin (Life Technologies), i.e., the constitutional ingredient 1) of the seven constitutional ingredients of the MSSC medium of Example 2, with a conditioned medium (a culture supernatant obtained after culturing CF1 cells with a medium obtained by replacing DMEM/F12 in a complete medium with knockout DMEM (supplemented with 20% knockout serum replacement (Invitrogen, USA), 1 mM glutamine, 1% nonessential amino acids (Invitrogen, USA), 0.1 mM β-mercaptoethanol, 0.1% penicillin-streptomycin and 5 mg/mL bovine serum albumin)) (the remaining constitutional ingredients 2)-7) are identical) was compared with that of the MSSC medium.

Noggin is generally used to maintain the characteristics of hESCs during culturing (Chaturvedi G, Simone P D, Ain R, Soares M J, Wolfe M W. Noggin maintains pluripotency of human embryonic stem cells grown on Matrigel. *Cell Prolif.* 2009 August; 42(4): 425-33). Contrarily to the previously known mechanism, it significantly increased the tendency toward the mesoderm. As can be seen from Table 1, the tendency for osteogenic differentiation was increased 10 times or greater when noggin was contained, as compared when the CM medium was used.

TABLE 1

Differentiation tendency of MSSC medium vs. CM medium
(number of observations out of 20 differentiations)

| Medium | Bone | Muscle | Tendon | Fat |
|---|---|---|---|---|
| CM medium | 1/20 | 20/20 | 2/20 | 2/20 |
| Noggin-containing medium | 15/20 | 20/20 | 10/20 | 12/20 |

Figure 6:
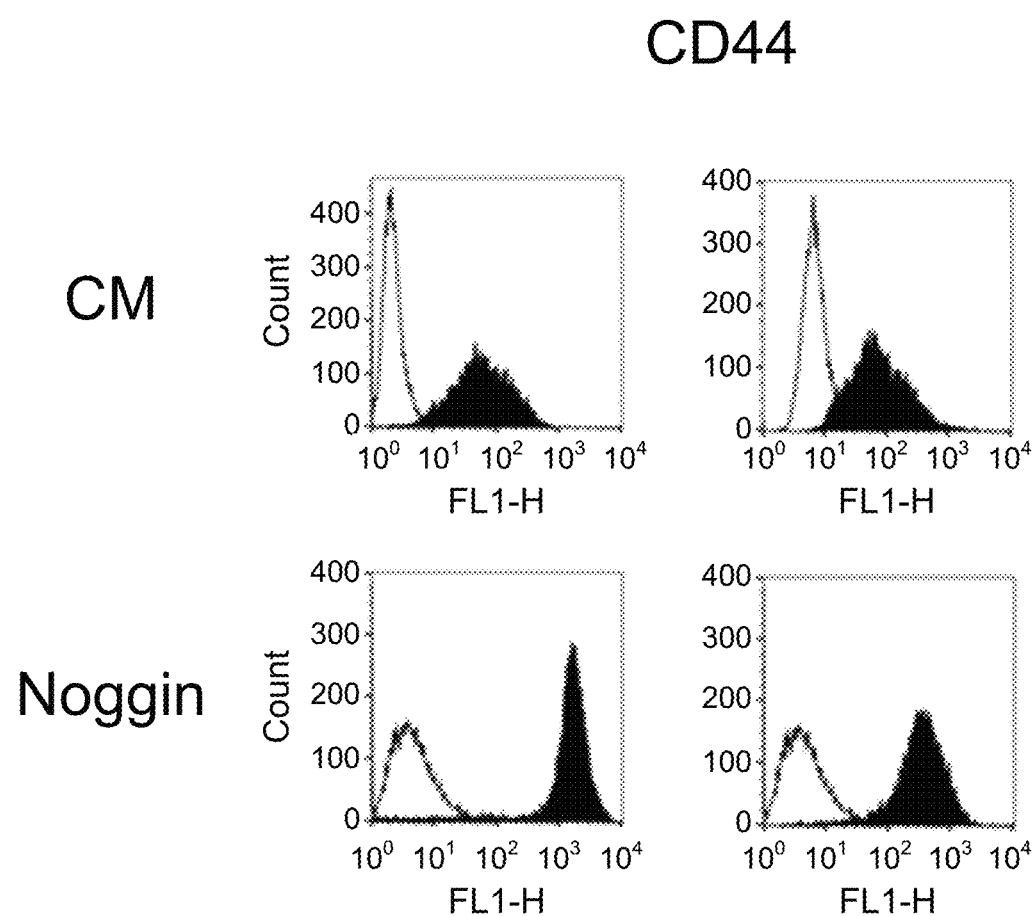
FIG. 6 shows a result of comparing the expression level of CD44 in a CM medium and in hMSSC differentiated using a medium for inducing differentiation into hMSSC by flow cytometry.

Also, the expression level of CD44 was compared for the two media. After inducing differentiation using the CM-containing medium (CM medium) and the noggin-containing medium (MSSC medium), the expression level of CD44 was measured in the same manner as in Example 6. As a result, it was confirmed that the expression level of CD44 was increased remarkably when the noggin-containing MSSC medium was used as compared to when the CM medium was used (FIG. 6).

During osteogenic differentiation, the formation of endochondral bone occurs only after chondrogenesis. CD44 is known to play an essential role in chondrogenesis (Wu S C, Chen C H, Chang J K, Fu Y C, Wang C K, Eswaramoorthy R, Lin Y S, Wang Y H, Lin S Y, Wang G J, Ho M L: Hyaluronan initiates chondrogenesis mainly via cd44 in human adipose-derived stem cells. *J Appl Physiol* (1985) 2013; 114: 1610-1618). From the above results, it can be seen that use of the MSSC medium rather than the CM medium is suitable for osteogenic differentiation.

When hMSSCs were transplanted into the kidney, the cells differentiated by the hMMSC medium showed 1-2 weeks faster differentiation as compared to the cells differentiated by the CM medium. The difference in differentiation speed when the CM medium was used and when the hMMSC medium was used is shown in Table 2.

TABLE 2

| mRNA level | | Week 1 | Week 2 | Week 3 | Week 4 |
|---|---|---|---|---|---|
| MYH9 | CM | 1.3 ± 0.1 | 2.1 ± 0.1 | 5.1 ± 0.3 | 12.5 ± 3.1 |
| | MSSC | 2.2 ± 0.3 | 4.4 ± 0.4 | 20.1 ± 3.1 | 23.1 ± 3.4 |
| Runx2 | CM | 1.2 ± 0.3 | 1.8 ± 0.3 | 3.6 ± 0.3 | 6.5 ± 3.1 |
| | MSSC | 2.1 ± 0.2 | 4.3 ± 0.3 | 7.1 ± 0.3 | 13.3 ± 3.1 |
| Scx | CM | 1.3 ± 0.2 | 2.3 ± 1.2 | 5.2 ± 1.3 | 10.7 ± 2.2 |
| | MSSC | 2.1 ± 0.2 | 4.7 ± 1.5 | 12.1 ± 0.3 | 16.5 ± 2.9 |

Differentiation speed of MSSC medium vs. CM medium (increased mRNA level as compared to before transplantation of hMSSC)

Comparative Example 2

Figure 7:
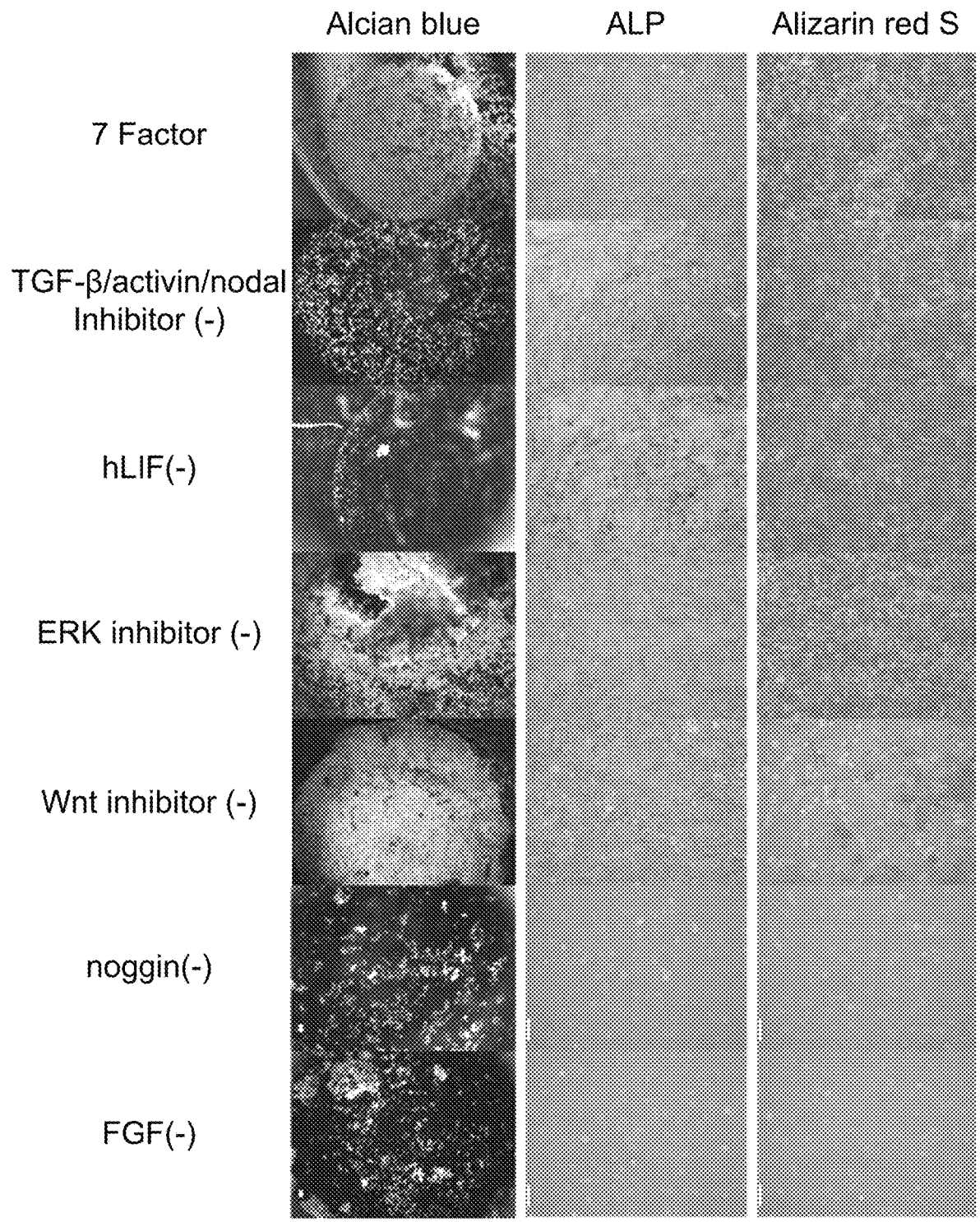
FIG. 7 shows a result of Alcian blue staining for confirming differentiation into cartilage and ALP and Alizarin red S staining for confirming differentiation into bone in order to investigate the tendency to differentiation into cartilage or bone when some ingredients are absent in a medium for inducing differentiation into hMSSC.

Comparison of Synergistic Effect for Combinations of Constitutional Ingredients of MSSC Medium The differentiation capacity of the MSSC medium of Example 2 not containing one of the constitutional ingredients 1)-6) was compared with that of the MSSC medium. As a result, it was confirmed that differentiation into cartilage (Alcian blue) or bone (ALP and Alizarin red S) was not achieved well when one of the constitutional ingredients 1)-6) was absent (FIG. 7, Table 3).

TABLE 3

Comparison of differentiation capacity of MSSC medium vs. medium deficient in one constitutional ingredient

| Constitutional ingredient of MSSC medium | 7 ingredients | TGF-β/ activin/ nodal signaling inhibitor (−) | hLIF (−) | ERK signaling inhibitor (−) | Wnt signaling activator (−) | Noggin (−) | FGF-2 signaling activator (−) |
|---|---|---|---|---|---|---|---|
| 1) Noggin | ○ | ○ | ○ | ○ | ○ | X | ○ |
| 2) LIF | ○ | ○ | X | ○ | ○ | ○ | ○ |
| 3) FGF-2 signaling activator | ○ | ○ | ○ | ○ | ○ | ○ | X |
| 4) Wnt signaling activator | ○ | ○ | ○ | ○ | X | ○ | ○ |
| 5) ERK signaling inhibitor | ○ | ○ | ○ | X | ○ | ○ | ○ |
| 6) TGF-β/ activin/ nodal signaling inhibitor | ○ | X | ○ | ○ | ○ | ○ | ○ |
| 7) Others | ○ | ○ | ○ | ○ | ○ | ○ | ○ |
| Remarks | Differentiated into muscle (including adipose), cartilage and bone | Not differentiated into muscle or cartilage | Not differentiated into cartilage | Differentiated into cartilage and bone was inhibited | Differentiated into bone was inhibited | MSSCs were not induced | MSSCs were not induced |

The invention claimed is:

1. A musculoskeletal stem cell (MSSC) differentiated from an ESC (embryonic stem cell) or an iPSC (induced pluripotent stem cell), wherein the musculoskeletal stem cell has the following characteristics:
   a) positive for the ectodermal marker nestin (NES);
   b) positive for the myogenic satellite marker Pax7;
   c) positive for the mesodermal marker α-SMA;
   d) negative for the pluripotency marker LIN28; and
   f) negative for the mesenchymal stem cell marker CD90
   wherein the musculoskeletal stem cell can be differentiated into bone, cartilage, tendon, ligament, muscle and fat.

2. The musculoskeletal stem cell according to claim 1, wherein the musculoskeletal stem cell is deposited in the Korean Cell Line Bank under the accession number KCLRF-BP-00460.

3. A pharmaceutical composition for preventing or treating a musculoskeletal disease, comprising the musculoskeletal stem cell according to claim 1.

4. The pharmaceutical composition according to claim 3, wherein the musculoskeletal disease is one or more disease selected from a group consisting of osteoporosis, osteomalacia, osteogenesis imperfecta, osteopetrosis, osteosclerosis, Paget's disease, bone cancer, arthritis, rickets, fracture, Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

periodontal disease, segmental bone defect, osteolytic bone disease, primary and secondary hyperparathyroidism, hyperostosis, degenerative arthritis, degenerative knee joint disease, degenerative hip joint disease, degenerative foot joint disease, degenerative hand joint disease, degenerative shoulder joint disease, degenerative elbow joint disease, chondromalacia patellae, simple knee arthritis, osteochondritis dissecans, lateral epicondylitis, medial epicondylitis, Heberden's nodes, Bouchard's nodes, degenerative thumb CM arthrosis, meniscal injury, degenerative disc disease, cruciate ligament injury, biceps brachii muscle injury, ligament injury, tendon injury, frozen shoulder, rotator cuff tear, calcific tendinitis, shoulder impingement syndrome, recurrent dislocation, habitual dislocation, senile sarcopenia and muscular dystrophy.

* * * * *